(12) United States Patent
Stoddart et al.

(10) Patent No.: US 12,084,579 B2
(45) Date of Patent: Sep. 10, 2024

(54) CYCLOPHANE-SUSTAINED HIGH PERFORMANCE PORPHYRINS

(71) Applicant: Northwestern University, Evanston, IL (US)

(72) Inventors: James Fraser Stoddart, Evanston, IL (US); Wenqi Liu, Evanston, IL (US)

(73) Assignee: Northwestern University, Evanston, IL (US)

( * ) Notice: Subject to any disclaimer, the term of this patent is extended or adjusted under 35 U.S.C. 154(b) by 15 days.

(21) Appl. No.: 17/445,057

(22) Filed: Aug. 13, 2021

(65) Prior Publication Data

US 2022/0049104 A1 Feb. 17, 2022

Related U.S. Application Data

(60) Provisional application No. 63/065,177, filed on Aug. 13, 2020.

(51) Int. Cl.
| | | |
|---|---|---|
| C09B 67/02 | (2006.01) | |
| C09B 67/48 | (2006.01) | |
| C09B 69/10 | (2006.01) | |
| G01N 21/64 | (2006.01) | |
| G01N 33/58 | (2006.01) | |

(52) U.S. Cl.
CPC ........ C09B 69/109 (2013.01); C09B 67/0025 (2013.01); G01N 21/6428 (2013.01); G01N 33/582 (2013.01); *G01N 2021/6439* (2013.01)

(58) Field of Classification Search
CPC ................................................ C09B 67/0025
See application file for complete search history.

(56) References Cited

U.S. PATENT DOCUMENTS

| | | |
|---|---|---|
| 8,273,875 B2 | 9/2012 | Smith et al. |
| 11,560,644 B2 * | 1/2023 | Stoddart ................. C30B 29/54 |

OTHER PUBLICATIONS

Liu et al. J. Am. Chem. Soc. 2020, 142, 8938-8945 and its supporting information (Year: 2020).*
Liu et al. J. Am. Chem. Soc. 2020, 142, 10273-10278 and its supporting information (Year: 2020).*
Mettry et al. Comprehensive Supramolecular Chemistry II, vol. 1, 2017, pp. 73-102 (Year: 2017).*
Dale et al. Acc. Chem. Res. 2016, 49, 262-273 (Year: 2016).*
Diederich, F. Modern Cyclophane Chemistry, Chapter 20, 2004, pp. 519-546 (Year: 2004).*
Persch, E.; Dumele, O.; Diederich, F. Molecular Recognition in Chemical and Biological Systems. Angew. Chem. Int. Ed. 2015, 54, 3290-3327.
Pettersen, E. F.; Goddard, T. D.; Huang, C. C.; Couch, G. S.; Greenblatt, D. M.; Meng, E. C.; Ferrin, T. E. UCSF Chimera—A Visualization System for Exploratory Research and Analysis. J. Comput. Chem. 2004, 25, 1605-1612.
Pluth, M. D.; Bergman, R. G.; Raymond, K. N. Making Amines Strong Bases: Thermodynamic Stabilization of Protonated Guests in a Highly-Charged Supramolecular Host. J. Am. Chem. Soc. 2007, 129, 11459-11467.
Polizzi, N. F.; Wu, Y.; Lemmin, T.; Maxwell, A. M.; Zhang, S. Q.; Rawson, J.; Beratan, D. N.; Therien, M. J.; DeGrado, W. F. De Novo Design of a Hyperstable Non-Natural Protein-Ligand Complex with Sub-Å Accuracy. Nat. Chem. 2017, 9, 1157-1164.
Qi, Q.; Yang, C.; Xia, Y.; Guo, S.; Song, D.; Su, H. Preferential Binding of π-Ligand Porphyrin Targeting 5'-5' Stacking Interface of Human Telomeric RNA G-Quadruplex Dimer. J. Phys. Chem. Lett. 2019, 10, 2143-2150.
Qiu, Y.; Zhang, L.; Pezzato, C.; Feng, Y.; Li, W.; Nguyen, M. T.; Cheng, C.; Shen, D.; Guo, Q. H.; Shi, Y.; Cai, K.; Alsubaie, F. M.; Astumian, R. D.; Stoddart, J. F. A Molecular Dual Pump. J. Am. Chem. Soc. 2019, 141, 17472-17476.
Rajora, M. A.; Lou, J. W. H.; Zheng, G. Advancing Porphyrin's Biomedical Utility via Supramolecular Chemistry. Chem. Soc. Rev. 2017, 46, 6433-6469.
Reedy, C. J.; Gibney, B. R. Heme Protein Assemblies. Chem. Rev. 2004, 104, 617-649.
Roy, I.; Bobbala, S.; Young, R. M.; Beldjoudi, Y.; Nguyen, M. T.; Cetin, M. M.; Cooper, J. A.; Allen, S.; Anamimoghadam, O.; Scott, E. A.; Wasielewski, M. R.; Stoddart, J. F. A Supramolecular Approach for Modulated Photoprotection, Lysosomal Delivery, and Photodynamic Activity of a Photosensitizer. J. Am. Chem. Soc. 2019, 141, 12296-12304.
Ryan, S. T. J.; Del Barrio, J.; Ghosh, I.; Biedermann, F.; Lazar, A. I.; Lan, Y.; Coulston, R. J.; Nau, W. M.; Scherman, O. A. Efficient Host-Guest Energy Transfer in Polycationic Cyclophane-Perylene Diimide Complexes in Water. J. Am. Chem. Soc. 2014, 136, 9053-9060.
Saleh, N.; Koner, A. L.; Nau, W. M. Activation and Stabilization of Drugs by Supramolecular pKa Shifts: Drug-Delivery Applications Tailored for Cucurbiturils. Angew. Chem. Int. Ed. 2008, 47, 5398-5401.
Schreiber, C. L.; Smith, B. D. Molecular Conjugation Using Non-Covalent Click Chemistry. Nat. Rev. Chem. 2019, 3, 393-400.
Sedghi, G.; Sawada, K.; Esdaile, L. J.; Hoffmann, M.; Anderson, H. L.; Bethell, D.; Haiss, W.; Higgins, S. J.; Nichols, R. J. Single Molecule Conductance of Porphyrin Wires with Ultralow Attenuation. J. Am. Chem. Soc. 2008, 130, 8582-8583.
Sheldrick, G. M. A Short History of SHELX. Acta Crystallogr. Sect. A 2008, 64, 112-122.
Sheldrick, G. M. SHELXT-Integrated Space-Group and Crystal-Structure Determination. Acta Crystallogr. Sect. A 2015, 71, 3-8.
Shetty, D.; Khedkar, J. K.; Park, K. M.; Kim, K. Can We Beat the Biotin-Avidin Pair?: Cucurbit[7]uril-Based Ultrahigh Affinity Host-Guest Complexes and Their Applications. Chem. Soc. Rev. 2015, 44, 8747-8761.

(Continued)

*Primary Examiner* — Matthew P Coughlin
(74) *Attorney, Agent, or Firm* — Quarles & Brady LLP

(57) ABSTRACT

Disclosed herein are receptor-substrate complexes comprising an octacationic tricyclic cyclophane and a pyrrole dye complexed therein and methods of using and making the same.

21 Claims, 11 Drawing Sheets

(56) References Cited

OTHER PUBLICATIONS

Song, X. Z.; Jaquinod, L.; Jentzen, W.; Nurco, D. J.; Jia, S. L.; Khoury, R. G.; Ma, J. G.; Medforth, C. J.; Smith, K. M.; Shelnutt, J. A. Metal Dependence of the Contributions of Low-Frequency Normal Coordinates to the Sterically Induced Distortions of Meso-Dialkyl-Substituted Porphyrins. Inorg. Chem. 1998, 37, 2009-2019.

Synthetic Receptors for Biomolecules: Design Principles and Applications, First Edition; Smith, B. D., Ed.; Royal Society of Chemistry, 2015.

Synytsya, A.; Synytsya, A.; Blafkova, P.; Volka, K.; Král, V. Interaction of Meso-tetrakis(4-sulphonatophenyl)porphine with Chitosan in Aqueous Solutions. Spectrochim. Acta Part A Mol. Biomol. Spectrosc. 2007, 66, 225-235.

Thordarson, P. Determining Association Constants from Titration Experiments in Supramolecular Chemistry. Chem. Soc. Rev. 2011, 40, 1305-1323.

Thorn, A.; Dittrich, B.; Sheldrick, G. M. Enhanced Rigid-Bond Restraints. Acta Crystallogr. Sect. A 2012, 68, 448-451.

Tromans, R. A.; Carter, T. S.; Chabanne, L.; Crump, M. P.; Li, H.; Matlock, J. V.; Orchard, M. G.; Davis, A. P. A Biomimetic Receptor for Glucose. Nat. Chem. 2019, 11, 52-56.

Tsutsui, T.; Kusaba, S.; Yamashina, M.; Akita, M.; Yoshizawa, M. Open Versus Closed Polyaromatic Nanocavity: Enhanced Host Abilities toward Large Dyes and Pigments. Chem. Eur. J. 2019, 25, 4320-4324.

Venema, F.; Rowan, A. E.; Nolte, R. J. M. Binding of Porphyrins in Cyclodextrin Dimers. J. Am. Chem. Soc. 1996, 118, 257-258.

Wang, A.; Ye, J.; Humphrey, M. G.; Zhang, C. Graphene and Carbon-Nanotube Nanohybrids Covalently Functionalized by Porphyrins and Phthalocyanines for Optoelectronic Properties. Adv. Mater. 2018, 30, 1-9.

Watanabe, K.; Kitagishi, H.; Kano, K. Supramolecular Iron Porphyrin/Cyclodextrin Dimer Complex that Mimics the Functions of Hemoglobin and Methemoglobin. Angew. Chem. Int. Ed. 2013, 52, 6894-6897.

Wolter, A. C.; Weickhmann, A. K.; Nasiri, A. H.; Hantke, K.; Ohlenschlager, O.; Wunderlich, C. H.; Kreutz, C.; Duchardt-Ferner, E.; Wöhnert, J. A Stably Protonated Adenine Nucleotide with a Highly Shifted pKaValue Stabilizes the Tertiary Structure of a GTP-Binding RNA Aptamer. Angew. Chem. Int. Ed. 2017, 56, 401-404.

Wu, Z. Q.; Li, C. Z.; Feng, D. J.; Jiang, X. K.; Li, Z. T. Foldamer-Based Pyridine-Fullerene Tweezer Receptors for Enhanced Binding of Zinc Porphyrin. Tetrahedron 2006, 62, 11054-11062.

Xue, X.; Lindstrom, A.; Li, Y. Porphyrin-Based Nanomedicines for Cancer Treatment. Bioconjug. Chem. 2019, 30, 1585-1603.

Yamashina, M.; Sartin, M. M.; Sei, Y.; Akita, M.; Takeuchi, S.; Tahara, T.; Yoshizawa, M. Preparation of Highly Fluorescent Host-Guest Complexes with Tunable Color Upon Encapsulation. J. Am. Chem. Soc. 2015, 137, 9266-9269.

Yang, L. P.; Wang, X.; Yao, H.; Jiang, W. Naphthotubes: Macrocyclic Hosts with a Biomimetic Cavity Feature. Acc. Chem. Res. 2019, 53, 198-208.

Yazaki, K.; Catti, L.; Yoshizawa, M. Polyaromatic Molecular Tubes: From Strategic Synthesis to Host Functions. Chem. Commun. 2018, 54, 3195-3206.

Yim, D.; Sung, J.; Kim, S.; Oh, J.; Yoon, H.; Sung, Y. M.; Kim, D.; Jang, W.-D. Guest-Induced Modulation of the Energy Transfer Process in Porphyrin-Based Artificial Light Harvesting Dendrimers. J. Am. Chem. Soc. 2016, 139, 993-1002.

Yin, H.; Cheng, Q.; Rosas, R.; Viel, S.; Monnier, V.; Charles, L.; Siri, D.; Gigmes, D.; Ouari, O.; Wang, R.; Kermagoret, A.; Bardelang, D. A Cucurbit[8]uril 2:2 Complex with a Negative pKa Shift. Chem. Eur. J. 2019, 25, 12552-12559.

Yoshizawa, M.; Catti, L. Bent Anthracene Dimers as Versatile Building Blocks for Supramolecular Capsules. Acc. Chem. Res. 2019, 52, 2392-2404.

Zhu, S. E.; Kuang, Y. M.; Geng, F.; Zhu, J. Z.; Wang, C. Z.; Yu, Y. J.; Luo, Y.; Xiao, Y.; Liu, K. Q.; Meng, Q. S.; Zhang, L.; Jiang, S.; Zhang, Y.; Wang, G. W.; Dong, Z. C.; Hou, J. G. Self-Decoupled Porphyrin with a Tripodal Anchor for Molecular-Scale Electroluminescence. J. Am. Chem. Soc. 2013, 135, 15794-15800.

Adam, S. M.; Wijeratne, G. B.; Rogler, P. J.; Diaz, D. E.; Quist, D. A.; Liu, J. J.; Karlin, K. D. Synthetic Fe/Cu Complexes: Toward Understanding Heme-Copper Oxidase Structure and Function. Chem. Rev. 2018, 118, 10840-11022.

Arunkumar, E.; Forbes, C. C.; Smith, B. D. Improving the Properties of Organic Dyes by Molecular Encapsulation. Eur. J. Org. Chem. 2005, 19, 4051-4059.

Bols, P. S.; Anderson, H. L. Template-Directed Synthesis of Molecular Nanorings and Cages. Acc. Chem. Res. 2018, 51, 2083-2092.

Börjesson, K.; Wiberg, J.; El-Sagheer, A. H.; Ljungdahl, T.; Mårtensson, J.; Brown, T.; Nordén, B.; Albinsson, B. Functionalized Nanostructures: Redox-Active Porphyrin Anchors for Supramolecular DNA Assemblies. ACS Nano. 2010, 4, 5037-5046.

Cao, L.; Šekutor, M.; Zavalij, P. Y.; Mlinarić-Majerski, K.; Glaser, R.; Isaacs, L. Cucurbit[7]uril • Guest Pair with an Attomolar Dissociation Constant. Angew. Chem. Int. Ed. 2014, 53, 988-993.

Cheng, C.; Cheng, T.; Xiao, H.; Krzyaniak, M. D.; Wang, Y.; McGonigal, P. R.; Frasconi, M.; Barnes, J. C.; Fahrenbach, A. C.; Wasielewski, M. R.; Goddard III, W. A.; Stoddart, J. F. Influence of Constitution and Charge on Radical Pairing Interactions in Tris-Radical Tricationic Complexes. J. Am. Chem. Soc. 2016, 138, 8288-8300.

Cheng, C.; McGonigal, P. R.; Schneebeli, S. T.; Li, H.; Vermeulen, N. A.; Ke, C.; Stoddart, J. F. An Artificial Molecular Pump. Nat. Nanotechnol. 2015, 10, 547-553.

Dale, E. J.; Vermeulen, N. A.; Thomas, A. A.; Barnes, J. C.; Juriek, M.; Blackburn, A. K.; Strutt, N. L.; Sarjeant, A. A.; Stern, C. L.; Denmark, S. E.; Stoddart, J. F. ExCage. J. Am. Chem. Soc. 2014, 136, 10669-10682.

Dempsey, J. M.; Zhai, C.; McGarraugh, H. H.; Schreiber, C. L.; Stoffel, S. E.; Johnson, A.; Smith, B. D. High Affinity Threading of a New Tetralactam Macrocycle in Water by Fluorescent Deep-Red and near-Infrared Squaraine Dyes. Chem. Commun. 2019, 55, 12793-12796.

Dolomanov, O. V; Bourhis, L. J.; Gildea, R. J.; Howard, J. A. K.; Puschmann, H. OLEX2: A Complete Structure Solution, Refinement and Analysis Program. J. Appl. Crystallogr. 2009, 42, 339-341.

Dsouza, R. N.; Pischel, U.; Nau, W. M. Fluorescent Dyes and Their Supramolecular Host/Guest Complexes with Macrocycles in Aqueous Solution. Chem. Rev. 2011, 111, 7941-7980.

Elemans, J. A. A. W.; Nolte, R. J. M. Porphyrin Cage Compounds Based on Glycolurile From Enzyme Mimics to Functional Molecular Machines. Chem. Commun. 2019, 55, 9590-9605.

Ethirajan, M.; Chen, Y.; Joshi, P.; Pandey, R. K. The Role of Porphyrin Chemistry in Tumor Imaging and Photodynamic Therapy. Chem. Soc. Rev. 2011, 40, 340-362.

Galan, A.; Ballester, P. Stabilization of Reactive Species by Supramolecular Encapsulation. Chem. Soc. Rev. 2016, 45, 1720-1737.

Ghosh, I.; Nau, W. M. The Strategic Use of Supramolecular pKa Shifts to Enhance the Bioavailability of Drugs. Adv. Drug Deliv. Rev. 2012, 64, 764-783.

Goto, Y.; Sugikawa, K.; Ikeda, A. Enhancement in Guest Molecule Incorporation into Lipid Membranes in the Presence of Zinc-Porphyrin Anchor Molecules. ChemistrySelect 2019, 4, 134-137.

Hagiwara, K.; Akita, M.; Yoshizawa, M. An Aqueous Molecular Tube with Polyaromatic Frameworks Capable of Binding Fluorescent Dyes. Chem. Sci. 2015, 6, 259-263.

Hargrove, A. E.; Zhong, Z.; Sessler, J. L.; Anslyn, E. V. Algorithms for the Determination of Binding Constants and Enantiomeric Excess in Complex Host : Guest Equilibria Using Optical Measurements. New J. Chem. 2010, 34, 348.

Houk, K. N.; Leach, A. G.; Kim, S. P.; Zhang, X. Binding Affinities of Host-Guest, Protein-Ligand, and Protein-Transition-State Complexes. Angew. Chem. Int. Ed. 2003, 42, 4872-4897.

Jia, F.; Hupatz, H.; Yang, L. P.; Schröder, H. V.; Li, D. H.; Xin, S.; Lentz, D.; Witte, F.; Xie, X.; Paulus, B.; Schalley, C. A.; Jiang, W. Naphthocage: A Flexible yet Extremely Strong Binder for Singly Charged Organic Cations. J. Am. Chem. Soc. 2019, 141, 4468-4473.

(56) References Cited

OTHER PUBLICATIONS

Juriček, M.; Barnes, J. C.; Strutt, N. L.; Vermeulen, N. A.; Ghooray, K. C.; Dale, E. J.; McGonigal, P. R.; Blackburn, A. K.; Avestro, A.-J.; Stoddart, J. F. An ExBox [2]Catenane. Chem. Sci. 2014, 5, 2724.
Kano, K.; Kitagishi, H.; Kodera, M.; Hirota, S. Dioxygen Binding to a Simple Myoglobin Model in Aqueous Solution. Angew. Chem. Int. Ed. 2005, 44, 435-438.
Ke, H.; Yang, L.-P.; Xie, M.; Chen, Z.; Yao, H.; Jiang, W. Shear-Induced Assembly of a Transient yet Highly Stretchable Hydrogel Based on Pseudopolyrotaxanes. Nat. Chem. 2019, 11, 470-477.
Kesters, J.; Verstappen, P.; Kelchtermans, M.; Lutsen, L.; Vanderzande, D.; Maes, W. Porphyrin-Based Bulk Heterojunction Organic Photovoltaics: The Rise of the Colors of Life. Adv. Energy Mater. 2015, 5, 1-20.
Kitagishi, H.; Tamaki, M.; Ueda, T.; Hirota, S.; Ohta, T.; Naruta, Y.; Kano, K. Oxoferryl Porphyrin/Hydrogen Peroxide System Whose Behavior Is Equivalent to Hydroperoxoferric Porphyrin. J. Am. Chem. Soc. 2010, 132, 16730-16732.
Kondo, K.; Akita, M.; Yoshizawa, M. Solubility Switching of Metallophthalocyanines and Their Larger Derivatives upon Encapsulation. Chem. Eur. J. 2016, 22, 1937-1940.
Koner, A. L.; Nau, W. M. Cucurbituril Encapsulation of Fluorescent Dyes. Supramol. Chem. 2007, 19, 55-66.
Kuang, G.; Zhang, Q.; Li, D. Y.; Shang, X. S.; Lin, T.; Liu, P. N.; Lin, N. Cross-Coupling of Aryl-Bromide and Porphyrin-Bromide on an Au(111) Surface. Chem. Eur. J. 2015, 21, 8028-8032.
Kubota, R.; Takabe, T.; Arima, K.; Taniguchi, H.; Asayama, S.; Kawakami, H. New Class of Artificial Enzyme Composed of Mn-Porphyrin, Imidazole, and Cucurbit[10]Uril toward Use as a Therapeutic Antioxidant. J. Mater. Chem. B 2018, 6, 7050-7059.
Kundu, S.; Patra, A. Nanoscale Strategies for Light Harvesting. Chem. Rev. 2017, 117, 712-757.
Lefebvre, C.; Rubez, G.; Khartabil, H.; Boisson, J. C.; Contreras-García, J.; Hénon, E. Accurately Extracting the Signature of Intermolecular Interactions Present in The NCI Plot of The Reduced Density Gradient Versus Electron Density. Phys. Chem. Chem. Phys. 2017, 19, 17928-17936.
Li, Z.; Borguet, E. Determining Charge Transport Pathways through Single Porphyrin Molecules Using Scanning Tunneling Microscopy Break Junctions. J. Am. Chem. Soc. 2012, 134, 63-66.
Liu, S.; Shukla, A. D.; Gadde, S.; Wagner, B. D.; Kaifer, A. E.; Isaacs, L. Ternary Complexes Comprising Cucurbit[10]uril, Porphyrins, and Guests. Angew. Chem. Int. Ed. 2008, 47, 2657-2660.
Liu, W.; Bobbala, S.; Stern, C. L.; Hornick, J. E.; Liu, Y.; Enciso, A. E.; Scott, E. A.; Stoddart, J. F. XCage: A Tricyclic Octacationic Receptor for Perylene Diimide with Picomolar Affinity in Water. J. Am. Chem. Soc. 2020, 142, 3165-3173 .
Liu, W.; Johnson, A.; Smith, B. D. Guest Back-Folding: A Molecular Design Strategy That Produces a Deep-Red Fluorescent Host/Guest Pair with Picomolar Affinity in Water. J. Am. Chem. Soc. 2018, 140, 3361-3370.
Liu, W.; Peck, E. M.; Smith, B. D. High Affinity Macrocycle Threading by a Near-Infrared Croconaine Dye with Flanking Polymer Chains. J. Phys. Chem. B 2016, 120, 995-1001.
Liu, W.; Samanta, S. K.; Smith, B. D.; Isaacs, L. Synthetic Mimics of Biotin/(Strept)Avidin. Chem. Soc. Rev. 2017, 46, 2391-2403.
Liu, Y.; Jin, J.; Deng, H.; Li, K.; Zheng, Y.; Yu, C.; Zhou, Y. Protein-Framed Multi-Porphyrin Micelles for a Hybrid Natural-Artificial Light-Harvesting Nanosystem. Angew. Chem. Int. Ed. 2016, 55, 7952-7957.
Lombardi, A.; Nastri, F.; Pavone, V. Peptide-Based Heme-Protein Models. Chem. Rev. 2001, 101, 3165-3189.
Lu, T.; Chen, F. Multiwfn: A Multifunctional Wavefunction Analyzer. J. Comput. Chem. 2012, 33, 580-592.
Mako, T. L.; Racicot, J. M.; Levine, M. Supramolecular Luminescent Sensors. Chem. Rev. 2019, 119, 322-477.
Merlau, M. L.; Mejia, M. D. .; Nguyen, S. T.; Hupp, J. T. Artificial Enzymes Formed through Directed Assembly of Molecular Square Encapsulated Epoxidation Catalysts. Angew. Chem. Int. Ed. 2001, 40, 4239-4242.
Milgrom, L. R. The Colours of Life: An Introduction to the Chemistry of Porphyrins and Related Compounds; Oxford University Press: Oxford New York Tokyo, 1997.
Mohanty, J.; Nau, W. M. Ultrastable Rhodamine with Cucurbituril. Angew. Chem. Int. Ed. 2005, 44, 3750-3754.
Moschetto, G.; Lauceri, R.; Gulino, F. G.; Sciotto, D.; Purrello, R. Non-Covalent Synthesis in Aqueous Solution of Discrete Multi-Porphyrin Aggregates with Programmable Stoichiometry and Sequence. J. Am. Chem. Soc. 2002, 124, 14536-14537.
Omagari, T.; Suzuki, A.; Akita, M.; Yoshizawa, M. Efficient Catalytic Epoxidation in Water by Axial N-Ligand-Free Mn-Porphyrins within a Micellar Capsule. J. Am. Chem. Soc. 2016, 138, 499-502.
Ono, K.; Yoshizawa, M.; Kato, T.; Watanabe, K.; Fujita, M. Porphine Dimeric Assemblies in Organic-Pillared Coordination Cages. Angew. Chem. Int. Ed. 2007, 46, 1803-1806.
Otsuki, J. Supramolecular Approach towards Light-Harvesting Materials Based on Porphyrins and Chlorophylls. J. Mater. Chem. A 2018, 6, 6710-6753.
Pathak, P.; Yao, W.; Hook, K. D.; Vik, R.; Winnerdy, F. R.; Brown, J. Q.; Gibb, B. C.; Pursell, Z. F.; Phan, A. T.; Jayawickramarajah, J. Bright G-Quadruplex Nanostructures Functionalized with Porphyrin Lanterns. J. Am. Chem. Soc. 2019, 141, 12582-12591.
Peck, E. M.; Liu, W.; Spence, G. T.; Shaw, S. K.; Davis, A. P.; Destecroix, H.; Smith, B. D. Rapid Macrocycle Threading by a Fluorescent Dye-Polymer Conjugate in Water with Nanomolar Affinity. J. Am. Chem. Soc. 2015, 137, 8668-8671.

* cited by examiner

CYCLOPHANE-SUSTAINED HIGH PERFORMANCE PORPHYRINS

CROSS-REFERENCE TO RELATED APPLICATIONS

This application claims benefit of priority to U.S. Application Ser. No. 63/065,177, filed Aug. 13, 2020, the contents of which is incorporated by reference in its entirety.

BACKGROUND OF THE INVENTION

Molecular recognition is utilized comprehensively by nature for the regulation of biological processes.[1,2] One of the goals in the supramolecular chemistry community is to make[3,4] synthetic receptors that can hold a candle to the binding affinities and functionalities of bioreceptors. In recent years, several wholly synthetic receptors have been reported[5,6] with substrate-binding affinities exceeding the performance of naturally occurring receptors. These high affinity synthetic receptors have shown[7] promising applications in drug delivery, membrane functionalization and protein purification. Advances in these biotechnologies create new and demanding requirements for synthetic receptors with, not only high binding affinities, but also with integrated[8-15] functionalities. It is desirable to develop high affinity receptors for functional substrates such as dye molecules.[16-19] Although there have been numerous reports[20-22] on dye encapsulations by several well-known receptors such as cyclodextrins, calixarenes, cucurbiturils and pillararenes, most of them fail to encapsulate dyes at nanomolar concentrations on account of their low binding affinities. Examples of high affinity receptors for functional dye molecules[23-27] are rare and are urgently needed[28] to meet the demanding requirement of biotechnologists and scientists working in related fields.

Porphyrins are indispensable dyes in biology and fulfill many crucial biological functions, such as oxygen transport, photosynthesis and metabolism.[29] Most porphyrins in nature exist as noncovalent complexes and are buried deep inside the superstructures of porphyrin-binding proteins, where their microenvironments, not only govern the versatile functions of porphyrins, but also protect them from direct interactions with solvents and solutes.[30] Much effort has been devoted to making synthetic mimics of these porphyrin-containing devices[30-32] and engineer them to express functions in artificial photodevices,[33,34] model enzymes[35-40] and biotechnologies.[41-43] To this end, one of our goals is to develop artificial receptors that bind strongly with porphyrins in confined microenvironments, in which we can modulate the photoelectrical properties and chemical reactivities of the encapsulated porphyrins.[4,8,44]

Binding of porphyrins has been explored using chemically modified proteins and peptides,[30,31,45] nucleotides[46,47] and other naturally derived compounds[48,49]. Porphyrins have also been substrates for intense targeting in the supramolecular community, where cyclodextrins,[50-52] calixarenes,[53] cucurbiturils,[54,55] cyclophanes,[56,57] foldamers[58] and coordination metal cages[39,59] have all been developed in order to interact with porphyrins with various functions in mind. Despite all these advances in mimicking porphyrin-binding proteins, the challenge remains to design a monomeric high-affinity receptor that can fully encapsulate porphyrins on account of their large sizes which exceed the cavity sizes of current synthetic receptors.[57]

BRIEF SUMMARY OF THE INVENTION

Disclosed herein are receptor-substrate complexes, or salts thereof, comprising an octacationic tricyclic cyclophane and a pyrrole dye complexed therein. The tricyclic octacationic cyclophane, or a salt thereof, may comprise a roof, a floor, and four pillars, wherein each of the roof and the floor are composed of a biphenyl unit having four pyridinium units extending therefrom and wherein each of the four pyridinium units of the roof are linked to another pyridinium unit of the floor by one of the four pillars. In some embodiments, the cyclophane is

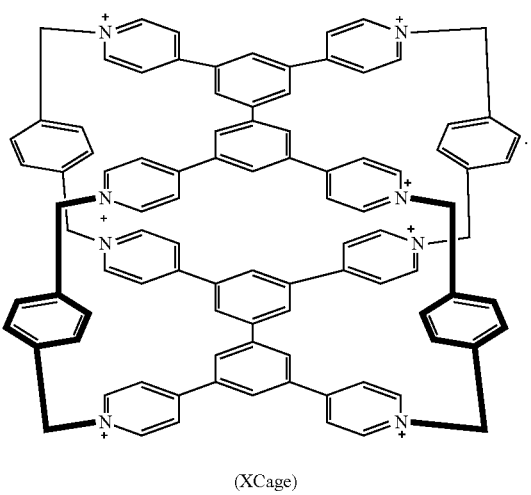

(XCage)

In some embodiments, the pyrrole dye is a porphyrin dye. In some embodiments, the pyrrole dye has a formula

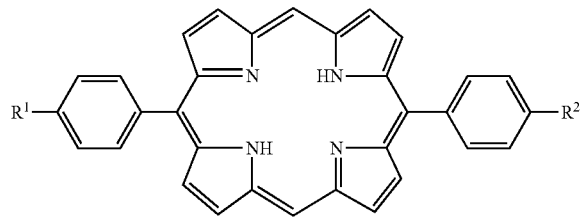

wherein $R^1$ and $R^2$ are independently selected from hydrogen, —OH, —NRR', —NO$_2$, —SH, —SR, —R, —OR, —COOR, —OCH$_2$CH$_2$(OCH$_2$CH$_2$)$_n$—OR, or —OCH$_2$-(triazole)-CH$_2$CH$_2$—(OCH$_2$CH$_2$)$_n$—OR, wherein each R and R' are independently selected from a substituted or unsubstituted, branched or unbranched, saturated or unsaturated $C_1$-$C_6$ alkyl, and wherein n is an integer greater than or equal to zero.

In some embodiments, the pyrrole dye is a metalloporphyrin dye. In some embodiments, the pyrrole dye has a formula

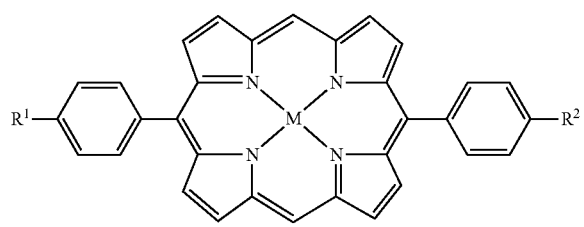

wherein $R^1$ and $R^2$ are independently selected from hydrogen, —OH, —NRR', —NO$_2$, —SH, —SR, —R, —OR, —COOR, —OCH$_2$CH$_2$(OCH$_2$CH$_2$)$_n$—OR, or —OCH$_2$-(triazole)-CH$_2$CH$_2$—(OCH$_2$CH$_2$)$_n$—OR, wherein each R and R' are independently selected from a substituted or unsubstituted, branched or unbranched, saturated or unsaturated $C_1$-$C_6$ alkyl, wherein n is an integer greater than or equal to zero, and wherein M is a transition metal or an alkaline earth metal.

Another aspect of the invention provides for crystalline composition comprising any of the complexes described herein.

Another aspect of the invention provides for method for fluorescence spectroscopy. The method may comprise providing any of the complexes described herein, irradiating the complex with an irradiation source, and detecting an emission signal from the complex.

Another aspect of the invention provides for a method for stabilizing a pyrrole dye. The method may comprise providing a tricyclic octacationic cyclophane, complexing the cyclophane with the pyrrole dye to prepare any of the complexes described herein.

Another aspect of the invention provides for methods for preparing any of the complexes disclosed herein. The method may comprise providing a tricyclic octacationic cyclophane, providing a pyrrole dye, and contacting the tricyclic octacationic cyclophane and the pyrrole dye.

These and other aspects of the invention will be further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

Figure 1:
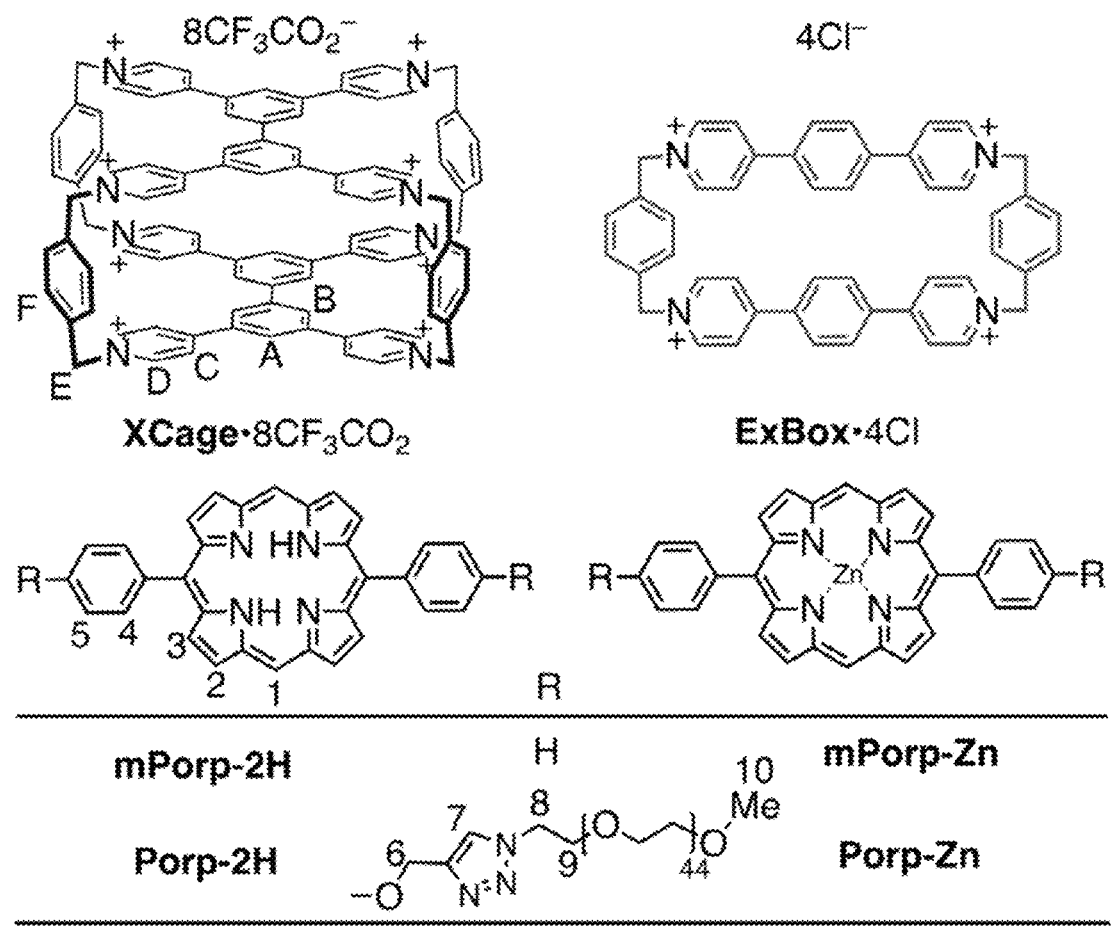
FIG. 1. Exemplary complexes and components thereof.

Disclosed herein are receptor-substrate complexes comprising encapsulated pyrrole dyes by an octacationic tricyclic cyclophane receptor with subnanomolar binding affinities in water. The high affinities are sustained by the hydrophobic effect and multiple [CH . . . π] interactions covering large [π . . . π] stacking surfaces between the substrate pyrrole and the receptor. We discovered two co-conformational isomers of the 1:1 complex, where the exemplary porphyrin is orientated differently inside the binding cavity of the receptor on account of its tricyclic nature. The photophysical properties and chemical reactivities of the encapsulated porphyrins are modulated to a considerable extent by the receptor. Improved fluorescence quantum yields, red-shifted absorptions and emissions, and nearly quantitative energy transfer processes highlight the emergent photophysical enhancements. The encapsulated porphyrins enjoy unprecedented chemical stabilities, where their D/H exchange, protonation, and solvolysis under extremely acidic conditions are completely blocked. The ultrahigh stabilities and improved optical properties of these encapsulated porphyrins will find applications in single-molecule materials, artificial photodevices and biomedical appliances.

The receptor-substrate complex comprises a pyrrole dye. Suitably macrocyclic pyrroles include, without limitation, porphyrins, chlorins, bacteriochlorins, phthalocyanines, naphthalocyanines, or subphthalocyanines. For example, the macrocylic pyrroles may be tetrapyrroles such as porphyrins (A), chlorins (B), and bacteriochlorins (C) having a core structure, respectively, of

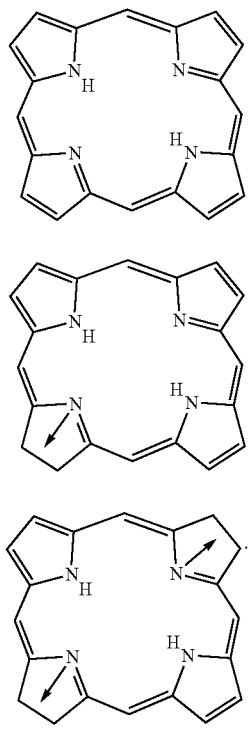

In some embodiments, a metal is bound to the core structure.

One or more substituents may be attached to the macrocyclic pyrrole core structure. In some embodiments, the pyrrole dye may have a formula of

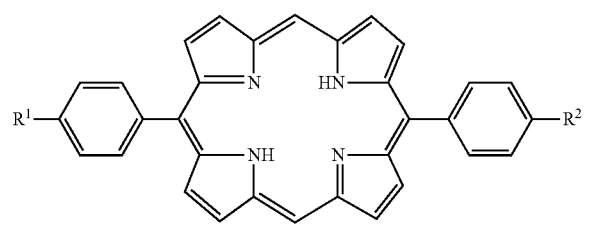

where $R^1$ and $R^2$ are independently selected from hydrogen, —OH, —NRR', —NO$_2$, —SH, —SR, —R, —OR, —COOR, —OCH$_2$CH$_2$(OCH$_2$CH$_2$)$_n$—OR, or —OCH$_2$-(triazole)-CH$_2$CH$_2$—(OCH$_2$CH$_2$)$_n$—OR and where each R and R' are independently selected from a substituted or unsubstituted, branched or unbranched, saturated or unsaturated $C_1$-$C_6$ alkyl and it is an integer greater than or equal to zero. In some embodiments, n is between 0 and 150. In other embodiments, the pyrrole dye may have a formula

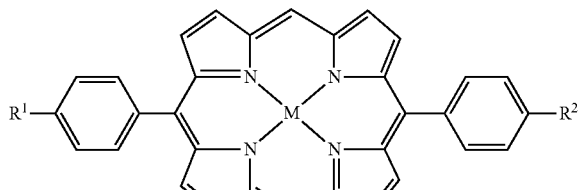

where $R^1$ and $R^2$ are independently selected from hydrogen, —OH, —NRR', —NO$_2$, —SH, —SR, —R, —OR, —COOR, —OCH$_2$CH$_2$(OCH$_2$CH$_2$)$_n$—OR, or —OCH$_2$-(triazole)-CH$_2$CH$_2$—(OCH$_2$CH$_2$)$_n$—OR and where each R and R' are independently selected from a substituted or unsubstituted, branched or unbranched, saturated or unsaturated $C_1$-$C_6$ alkyl, n is an integer greater than or equal to zero and M is a metal, such as a transition metal or an alkaline earth metal. In some embodiments, it is between 0 and 150. Suitably, M may be Zn, Au, Pd, Pt, Cu, Ni, Mg, Fe, Mn, Co, or any other suitable metal that can bind to the macrocycle.

Exemplary pyrrole dyes include, without out limitation:

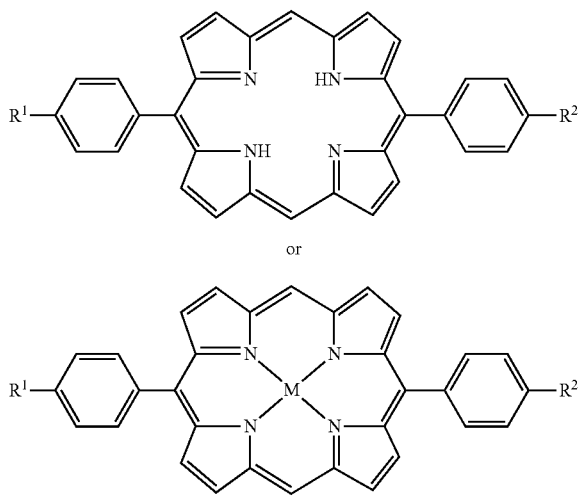

or where $R^1$ and/or $R^2$ are independently selected from

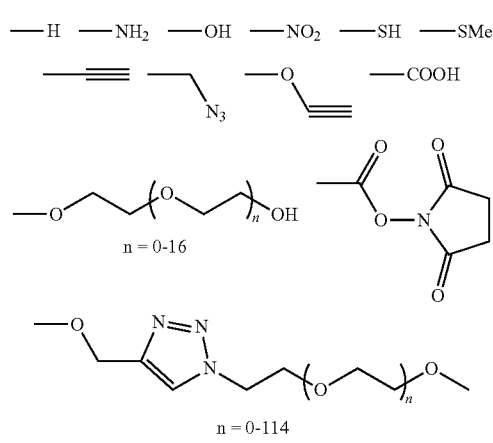

-continued

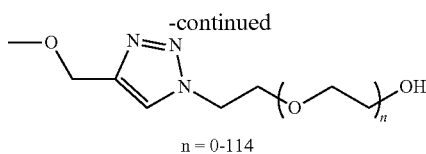

n = 0-114 and M, if present, is Zn, Au, Pd, Pt, Cu, Ni, Mg, Fe, Mn, or Co.

The receptor is a tricyclic octacationic cyclophane receptor featuring a roof-pillar-floor structure. Each of the roof and the floor are composed of a biphenyl unit having four pyridinium units extending therefrom. Pillars connect a pyridinium unit of the roof with another pyridinium unit of the floor. The biphenyl unit provides a large and flat binding surface, and four pillars connecting each of the four pyridinium units of the roof with another pyrinium unit of the floor results in a rigid cavity capable of hosting a dye substrate. The eight cationic pyridinium units provide both sufficient water solubility and complementary electronic binding sites for electron-rich moieties such as carbonyl groups. In some embodiments, the pillars comprise a xylylene unit.

In some embodiments, the cyclophane is

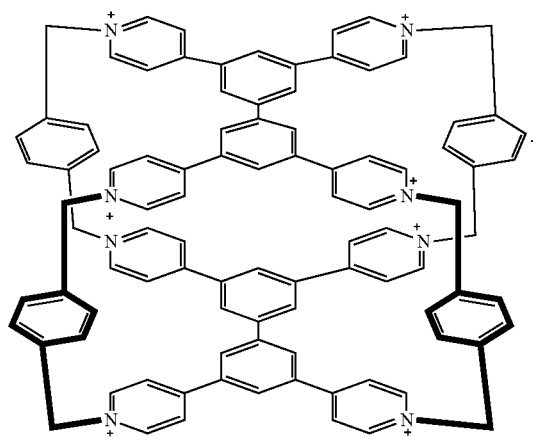

This cyclophane is referred to as XCage$^{8+}$ in view of its X-shaped structure. Four p-xylylene units serve as pillars with the ideal lengths (7.0 Å) to support aromatic [π . . . π] stacking interactions (2×3.5 Å) with an aromatic substrate, such as a PDI dye, in its cavity.

Salts of the receptor and receptor-substrate complex are also provided. The salt comprises a counter anion to balance the charge of the receptor or receptor-substrate complex. In some embodiments, the counter anion is an anion that is tolerated by cellular or living systems to allow for imaging of living systems. In some embodiments, the counter anion is $CF_3CO_2^-$, $PF_6^-$, or $Cl^-$.

The receptor features a large and rigid binding cavity. The constitution of the receptor exhibits high stereoelectronic complementarity toward pyrrole dyes with subnanomolar binding affinities. These ultrahigh affinities can be attributed to multiple [CH . . . π] interactions in addition to large [π . . . π] stacking surfaces between the substrate porphyrins and the receptor XCage$^{8+}$. Two types of co-conformational isomers, in which the porphyrin substrates are orientated differently inside the binding cavity of XCage$^{8+}$, were uncovered by $^1H$ NMR spectroscopy in $D_2O$. The photo-physical properties of the encapsulated porphyrins turn out to be modulated by XCage$^{8+}$. Improved fluorescence quantum yields, red-shifted absorptions and emissions, and a nearly quantitative energy transfer process are all observed. In addition to these physical attributes, the encapsulated porphyrins show remarkable chemical stabilities, reflected in the fact that their protonation, D/H exchange, and solvolysis under extremely acidic conditions, are blocked.

X-Ray Crystallographic Analysis

Figure 2:
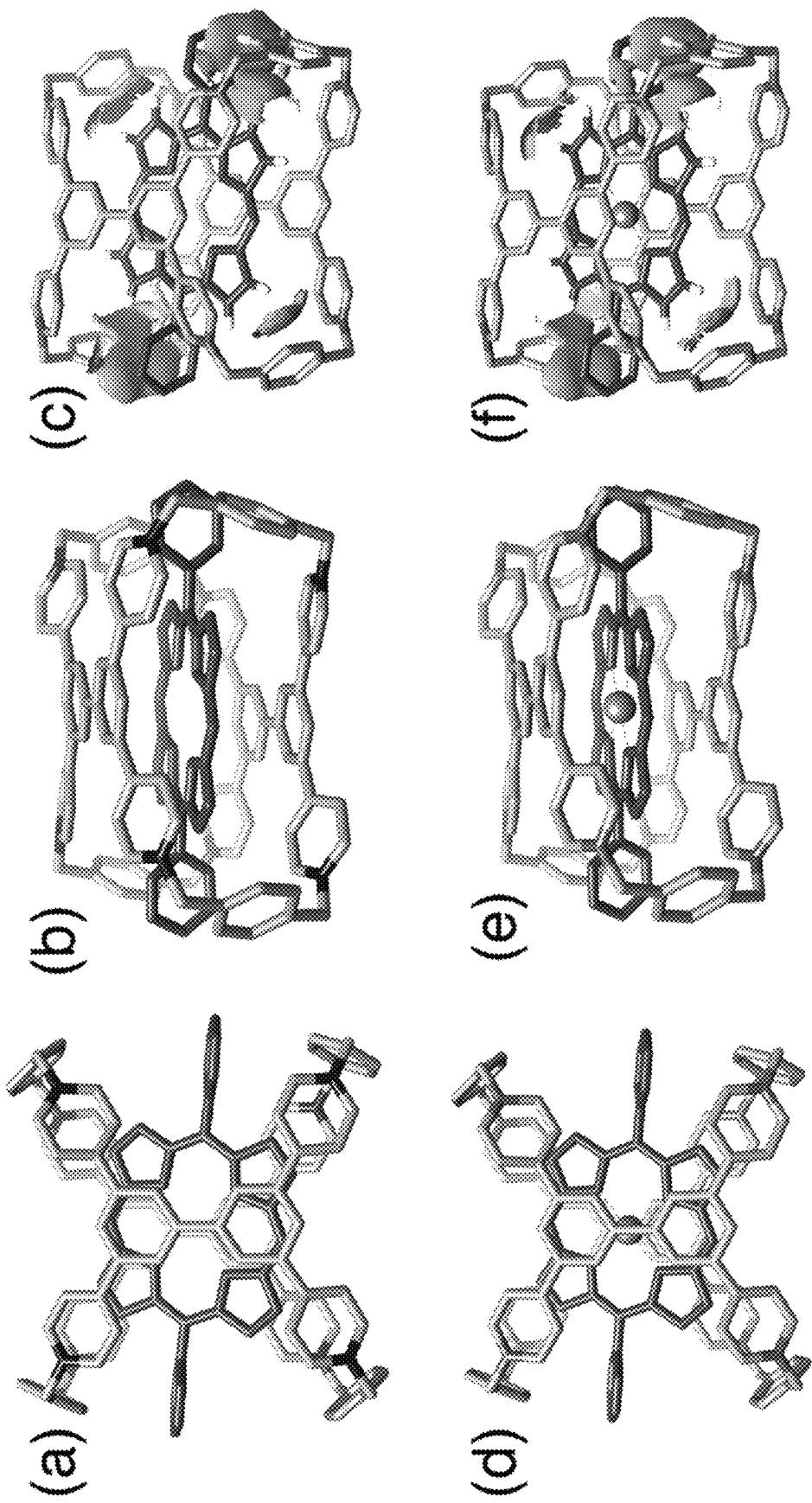
FIG. 2. Stick representation of the solid-state superstructures obtained from single-crystal X-ray crystallography. (a) Top-down view, (b) side-on view and (c) [CH . . . π] binding surfaces of mPorp-2H⊂XCage$^{8+}$. (d) Top-down view, (e) side-on view and (f) [CH . . . π] binding surfaces of mPorp-Zn⊂XCage$^{8+}$ FIG. 3. Co-conformational isomer transformation in D$_2$O solution tracked by dynamic $^1$H NMR spectroscopy. (a) Molecular models illustrating the transformation of co-conformer V to H. (b) $^1$H NMR (500 MHz, D$_2$O, 25° C.) Spectra of mPorp-2H⊂XCage$^{8+}$ collected at 0, 48 and 72 h at room temperature, along with additional heating at 70° C. for 5 and 24 h. * designates $^1$H NMR signals for the coconformer V of mPorp-2H⊂XCage$^{8+}$ FIG. 4. $^1$H NMR Spectroscopic investigation of the formation of the Porp-2H⊂XCage$^{8+}$ complex. (a) $^1$H NMR (500 MHz, D$_2$O, 25° C.) spectra of (top) the equilibrated Porp-2H⊂XCage$^{8+}$ and (bottom) XCage$^{8+}$. (b) $^1$H-$^1$H NOESY (500 MHz, D$_2$O, 25° C., 0.2 s mixing time) of the equilibrated Porp-2H⊂XCage$^{8+}$. Proton labels are defined on the relevant structural formulas in FIG. 1
Figure 8:
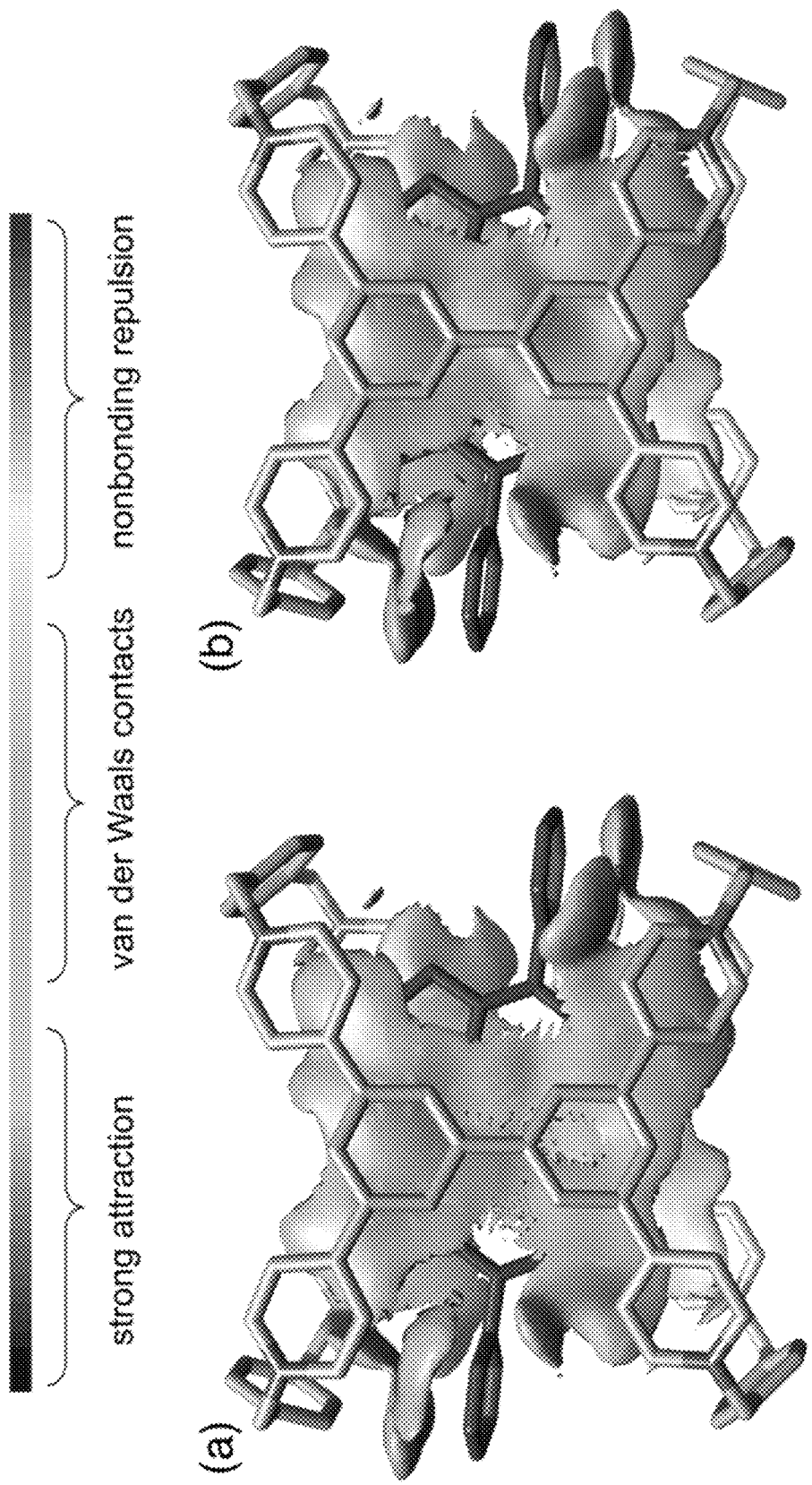
FIG. 8. Intermolecular binding iso-surface of (a) mPorp-2H⊂XCage$^{8+}$ and (b) mPorp-Zn⊂XCage$^{8+}$. Δκ inter (ρ)=0.003 a.u. Iso-surfaces are shaded according to a BGR scheme over the range −0.05<sign(λ2)ρ<+0.05 a.u. Scale bar: shading codes for noncovalent bonding surfaces predicted by IGM analysis FIG. 9. Change of fluorescent intensity (ex: 450 nm) over time upon the addition of XCage$^{8+}$ (1 μM) into a solution of Porp-2H (1 μM) in 1120 and its corresponding non-linear fitting curve for the determination of kinetics constant $k_{on}$ FIG. 10. Change of fluorescent intensity (ex: 402 nm) over time upon the addition of XCage$^{8+}$ (1 μM) into a solution of Porp-Zn (1 μM) in H$_2$O and its corresponding non-linear fitting curve for the determination of kinetics constant $k_{on}$ FIG. 11. Absorption spectra of (a) Porp-Zn and (b) Porp-Zn⊂XCagesin H$_2$O (5) and 1M HCl (6). Spectra were collected at 2 μM FIG. 12. Absorption spectra of (a) Porp-2H⊂ExBox$^{4+}$ and (b) Porp-Zn⊂ExBox$^{4+}$ in H$_2$O (7) and 1M HCl (8). Spectra were collected at 2 μM

A preliminary evaluation of the porphyrin binding capability using XCage$^{8+}$ was performed by X-ray crystallography. A mixture of the model compounds mPorp-2H(Zn) with XCage$^{8+}$ results (FIG. 1) in the solubilization of these porphyrins in water, a good indication of complex formation. Single crystals were obtained by slow diffusion of $iPr_2O$ into $Me_2CO$ solutions of these complexes. In the superstructures of mPorp-2H(Zn) ⊂ XCage$^{8+}$, both mPorp-2H and mPorp-Zn are positioned (FIG. 2) horizontally with respect to the binding cavity of XCage$^{8+}$. The diphenyl roof and floor of XCage$^{8+}$ show large areas of [π . . . π] stacking with the porphyrin cores. Furthermore, there are multiple [CH . . . π] interactions between the four p-xylylene pillars of XCage$^{8+}$ and the porphyrin. These [CH . . . π] distances range from 2.9 to 4.4 Å. The noncovalent bonding interactions were visualized (FIG. 8) by using the independent gradient model (IGM) analysis.[60]

NMR Spectroscopy in Solution

Figure 3:
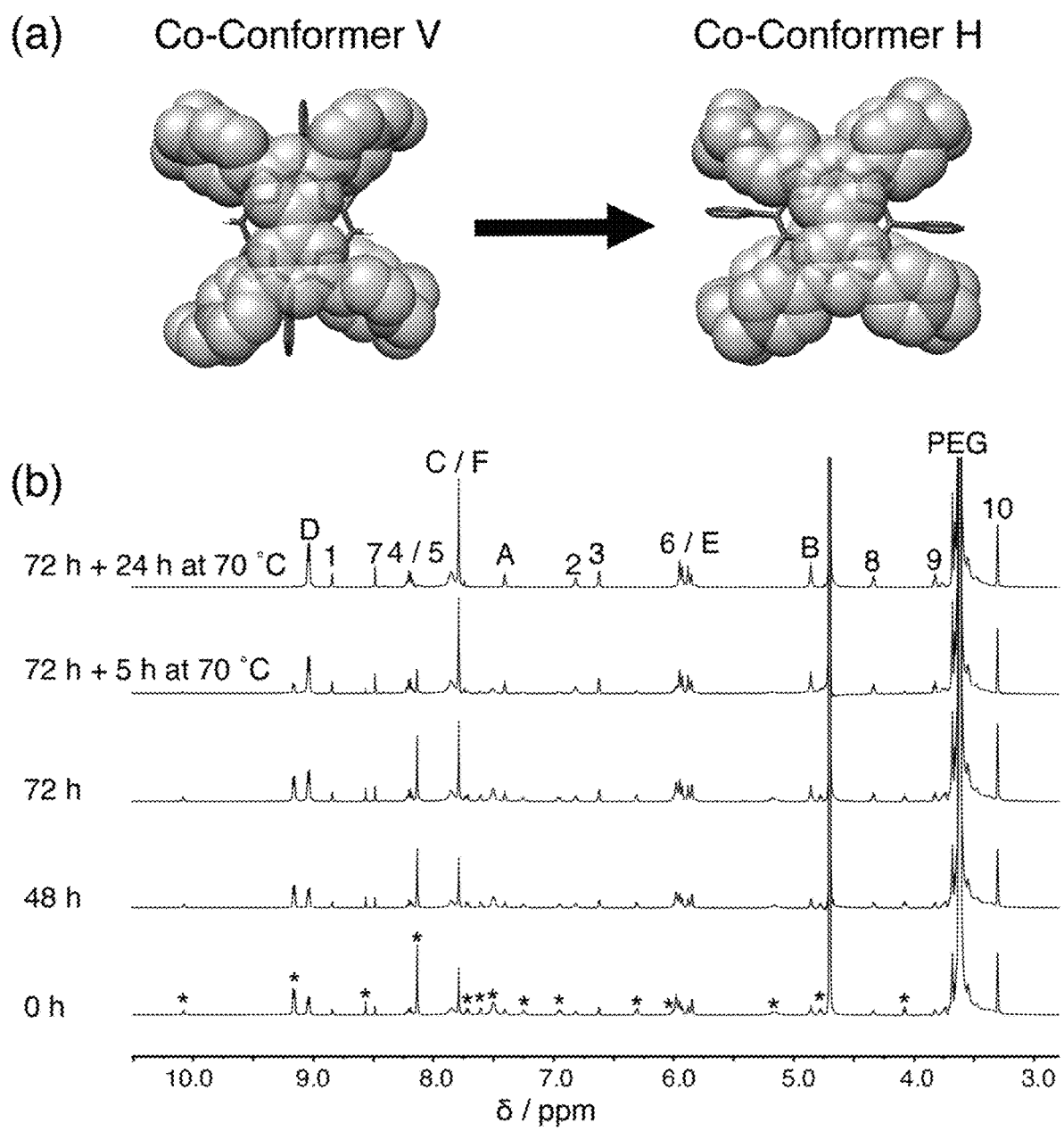

Both mPorp-2H and mPorp-Zn are insoluble in water, preventing the carrying out quantitative binding studies. In order to evaluate the receptor-substrate binding in solution, two water-soluble porphyrins (Porp-2H and Porp-Zn), flanked by polydispersed PEG chains, were synthesized using standard protocols. Upon mixing XCage$^{8+}$ with Porp-2H(Zn) in $D_2O$, the complexes formed quantitatively as indicated by the $^1H$ NMR spectra. Surprisingly, two sets of proton signals for the encapsulated porphyrins are observed (FIG. 3), indicating the presence of two co-conformational isomers. One set of $^1H$ NMR signals corresponds to co-conformer H as defined by X-ray crystallography. The other set of $^1H$ NMR signal most likely originates from co-conformer V in which the porphyrin substrate is located vertically in relation to the binding cavity of XCage$^{8+}$. The meso protons (1) of the porphyrin are obscured by XCage$^{8+}$ in co-conformer H, and their chemical shift appears at 8.8 ppm as a result of the shielding effects by the diphenyl units. In contrast, the meso protons (1) in co-conformer V are beyond the coverage of XCage$^{8+}$; thus, their chemical shift shows up at 10.1 ppm. By comparing integrations, we found that the ratio of co-conformer V to co-conformer H is 6:4 and 4:6, respectively for Porp-2H ⊂ XCage$^{8+}$ and Porp-Zn ⊂ XCage$^{8+}$. Co-conformer V represents a kinetically trapped metastable state, which is gradually transformed into co-conformer H over time. It takes 72 h at room temperature to complete the transformation in the case of Porp-Zn ⊂ XCage$^{8+}$. The transformation of Porp-2H ⊂ XCage$^{8+}$ is more difficult to achieve and requires additional heating at 70° C. for 24 h to form the co-conformer H. This observation differs from the previously reporte[27] PDI ⊂ XCage$^{8+}$ complex, where the substrate PDI is only observed as being positioned vertically with respect to the binding cavity of XCage$^{8+}$. The co-existence of co-conformers H and V can be attributed to the square-shaped porphyrin core, which presents a similar overlapping surface area with XCage$^{8+}$ in both co-conformers. The phenyl groups in the porphyrin are expected to experience unfavorable steric strain in co-conformer V, making it a less stable species when compared with co-conformer H, where the phenyl groups actually contribute to the overall stability of the complex by supporting several [CH . . . π] interactions with XCage$^{8+}$. While controlling the transformation of these two co-conformers is beyond the scope of this investigation, it is worth noting that this type of co-conformational isomerization could lead to new opportunities to manipulate multiple binding states within a multicyclic receptor.

Figure 4:
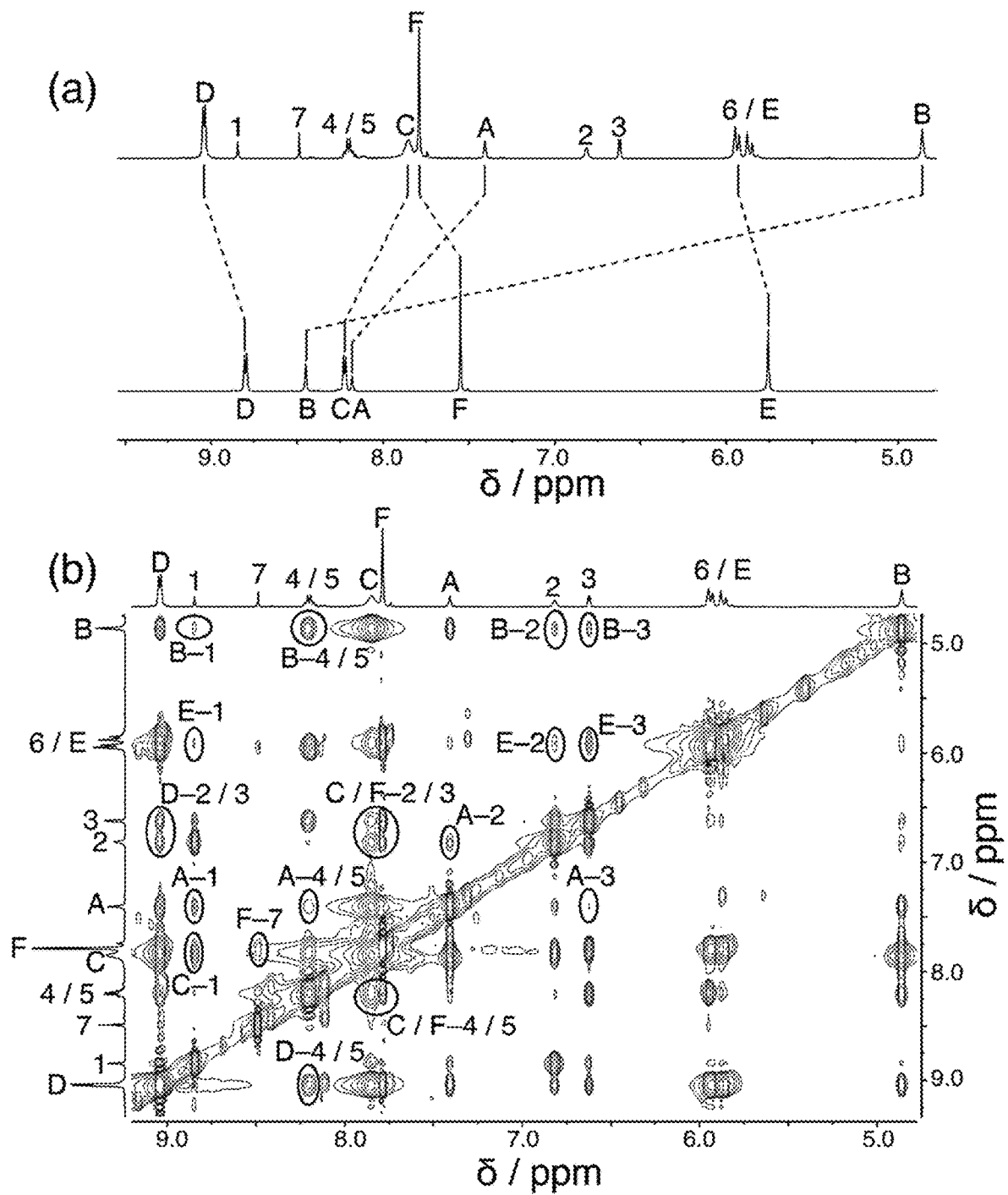

The $^1$H NMR spectrum of the equilibrated Porp-2H ⊂ XCage$^{8+}$ in D$_2$O reveals (FIG. 3) distinctive peaks for porphyrin units as co-conformer H. The amphiphilic nature of Porp-2H and Porp-Zn leads to their aggregation in D$_2$O, causing the proton resonances in prophyrins to be masked. Protons D, E, F on XCage$^{8+}$ experience the deshielding effect of the aromatic porphyrin ring and are downfield shifted. Protons A and C, which are positioned within the porphyrin shielding region, experience upfield shifts. Protons B, facing the shielding center of the porphyrin ring, experience the most dramatic upfield shift (Δδ=−3.6 ppm). A NOESY experiment confirmed (FIG. 4) the encapsulated structure by showing the expected through-space correlation peaks between Porp-2H and XCage$^{8+}$. Since no NOE signal is observed between the long PEG chains and XCage$^{8+}$, these chains do not contribute to the overall stability of the complexes. It is worthy of note that the triazole rings are also likely to participate in binding with XCage$^{8+}$, as revealed by the through-space correlations between the triazole ring protons 7 and protons F. Such a guest-backfolding phenomenon has been reported[23,63,64] previously to stabilize non-covalent complexes. The corresponding $^1$H NMR spectroscopic analysis of Porp-Zn ⊂ XCage$^{8+}$ is described in the Supporting Information.

Photophysical Properties

Figure 5:
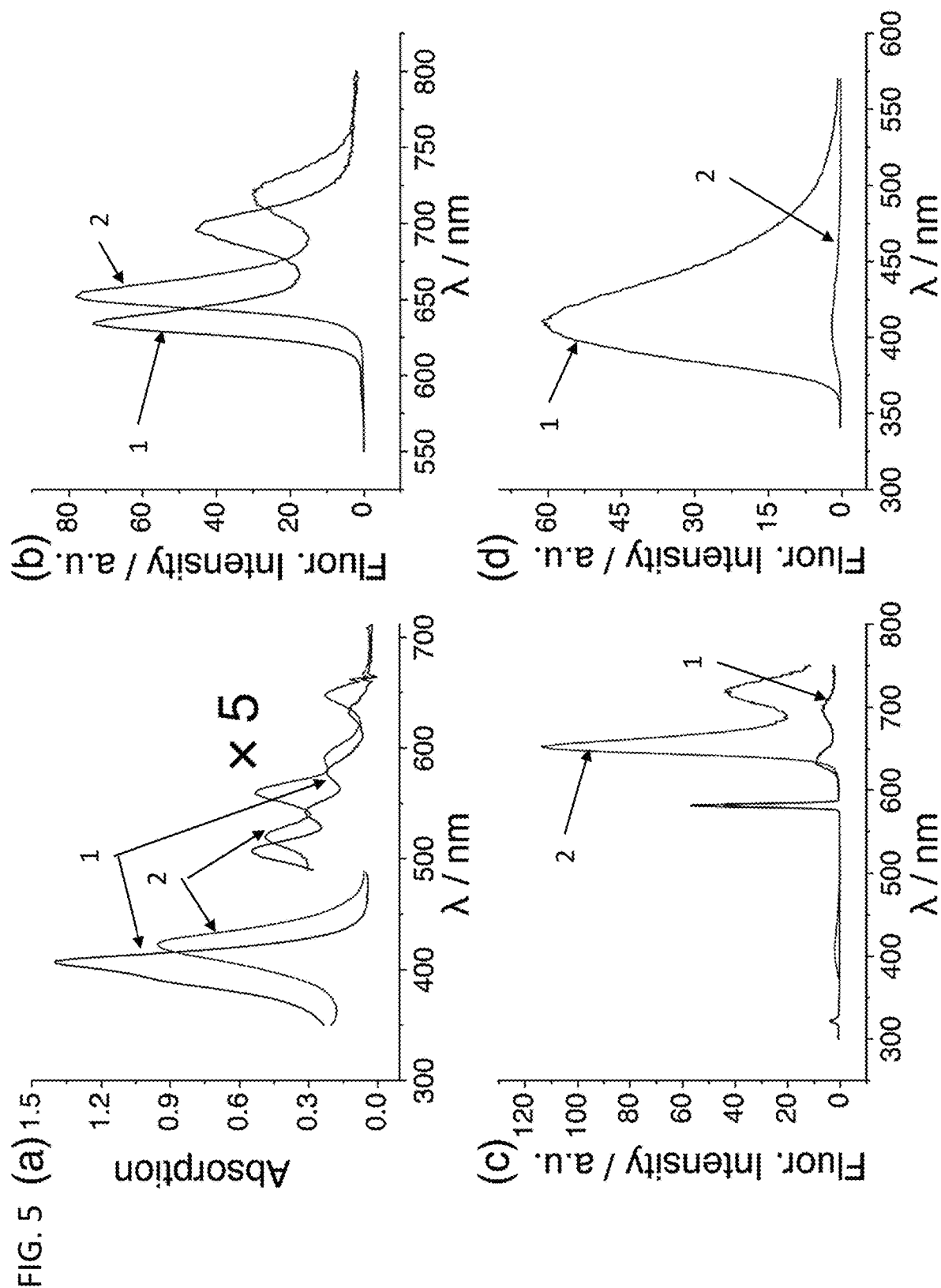
FIG. 5. Steady-state absorption and emission spectra. (a) Absorption and (b) emission (ex: 440 nm) spectra of Porp-2H (1)(10 μM) and Porp-2H⊂XCage$^{8+}$ (2)(10 μM). (c) Emission spectra (ex: 290 nm) of Porp-2H (1) (1 μM) and Porp-2H⊂XCage$^{8+}$ (2) (1 μM). (d) Emission spectra (ex: 330 nm) of XCage$^{8+}$ (1)(1 μM) and Porp-2H⊂XCage$^{8+}$ (2)(1 μM). All spectra were collected in H$_2$O at 25° C.

The association between Porp-2H(Zn) and XCage$^{8+}$ induces characteristic changes in their optical properties. Red-shifted absorption and emission (FIG. 5 panels (a) and (b)) of the encapsulated Porp-2H were observed, and its fluorescence quantum yield was enhanced from 16 to 25%, benefiting from the porphyrin being isolated in the hydrophobic binding pocket of XCage$^{8+}$. In comparison, previously reported porphyrin receptors either quench[57] the fluorescence or fail to induce any photophysical response.[55] The encapsulation of Porp-Zn by XCage$^{8+}$ decreases the fluorescence quantum yield from 5 to 0.6%.

There is an efficient energy transfer process from XCage$^{8+}$ to Porp-2H. When excited at 290 nm, the complex exhibits (FIG. 5 panel (c)) strong emission peaks for the Porp-2H ⊂ XCage$^{8+}$ complex at 650 nm. The energy transfer efficiency was estimated by comparing (FIG. 5 panel (d)) the fluorescence emission spectra of XCage$^{8+}$ and Porp-2H ⊂ XCage$^{8+}$ excited at 330 nm. The close-to-complete fluorescence quenching of XCage$^{8+}$ in the complex of Porp-2H ⊂ XCage$^{8+}$ is a compelling sign of the efficient energy transfer, which is calculated to be >96%. Time-dependent DFT calculations carried out on Porp-2H ⊂ XCage$^{8+}$ reveal that the HOMO is localized on Porp-2H and the LUMO on XCage$^{8+}$. The calculated UV-Vis absorption spectrum of Porp-2H ⊂ XCage$^{8+}$ is red-shifted compared with that of Porp-2H, which is in agreement with experimental observations.

Figure 6:
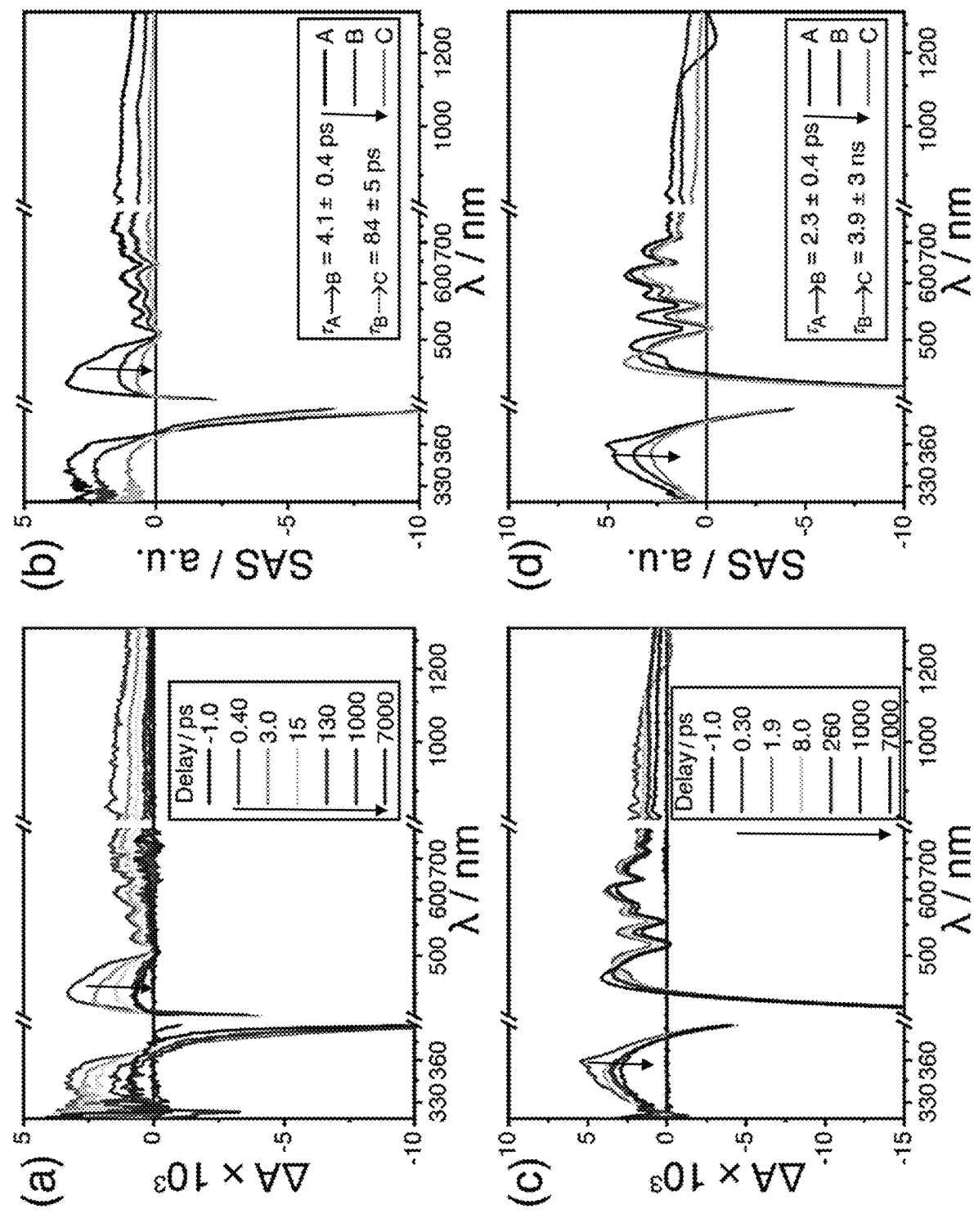
FIG. 6. Femtosecond transient absorption spectroscopy. Femtosecond TA spectra of (a) Porp-2H and (c) Porp-2H⊂XCage$^{8+}$ in H$_2$O excited at 414 nm. Species-associated spectra of (b) Porp-2H and (d) Porp-2H⊂XCage$^{8+}$ obtained by wavelength global fitting to an A→B→C kinetic model. State A represents the higher singlet excited state $S_2$ $^1$°Porp-2H, state B is the lowest singlet excited state $S_1$ $^1$°Porp-2H, and state C is the triplet state $T_1$ $^3$°Porp-2H. State C in (d) is not fully resolved on account of the slow ISC rate FIG. 7. Stability test of Porp-2H and Porp-2H⊂XCage$^{8+}$. Absorption spectrum of (a) Porp-2H and (b) Porp-2H⊂XCage$^{8+}$ in H$_2$O (3) and 1M HCl (4). Inserts showing the corresponding solution in H$_2$O (left) and HCl (right). (c) $^1$H NMR (500 MHz, D$_2$O, 25° C.) spectrum of the preassembled Porp-2H⊂XCage$^{8+}$ in D$_2$O.

In order to gain a better understanding of the influence of molecular encapsulation on photophysical properties, transient absorption (TA) experiments were performed at femtosecond and nanosecond resolutions. Femtosecond TA studies, exciting the Soret band at 414 nm, reveal (FIG. 6) a significant enhancement of the lifetime of intersystem crossing when Porp-21H is encapsulated in the cavity of XCage$^{8+}$. This result corroborates the enhanced fluorescence quantum yield of Porp-2H ⊂ XCage$^{8+}$. Compared to Porp-2H, Porp-2H ⊂ XCage$^{8+}$ shows improved stability of the triplet state as revealed by the nanosecond TA spectra. The energy transfer within Porp-2H ⊂ XCage$^{8+}$ was investigated by femtosecond TA spectroscopy using an excitation wavelength of 330 nm. Under these conditions, we only observe the excited state of Porp-2H, and no excited state of XCage$^{8+}$ could be detected within 0.4 ps, suggesting an ultrafast rate of energy transfer (data not shown), which corroborate the efficient energy transfer process observed by the fluorescence emission spectroscopy. In contrast to Porp-2H ⊂ XCage$^{8+}$, femtosecond TA spectra of Porp-Zn ⊂ XCage$^{8+}$ shows a charge-separated state, accounting for the decreased fluorescence of this complex.

Binding Thermodynamics and Kinetics

The changes in optical properties upon porphyrin encapsulation enable a facile study of the binding events. Fluorescence titrations of Porp-2H and Porp-Zn with ExBox$^{4+}$ yielded directly their binding constants in water. Since the binding affinities for XCage$^{8+}$ with Porp-2H and Porp-Zn are too high to be determined directly, competitive titrations were performed by displacing ExBox$^{4+}$ with XCage$^{8+}$ from the complex Porp-2H(Zn) ⊂ ExBox$^{4+}$. The binding affinities (Table 1) between ExBox$^{4+}$ and the two porphyrins are in the order of $10^7$ M$^{-1}$. Compared with ExBox$^{4+}$, XCage$^{8+}$ shows around a 1000-fold enhancement in the binding affinities, which are around $10^{10}$ M$^{-1}$ ($K_d$=0.1 nM). The highest affinity ($K_a$=1.7×$10^{10}$ M$^{-1}$) was achieved in the binding between XCage$^{8+}$ and Porp-2H. It should be noted that these $K_a$ values are interpreted as a lower limit to the stability constant, as the measurement was performed under conditions where co-conformers V and H coexist in solution. The samples were equilibrated for 6 h prior to the fluorescence titration studies. Based on time-dependent $^1$H NMR spectroscopic experiments, the transformation of co-conformer V to H requires 72 h or longer to reach completion. The equilibrated co-conformer H is expected to have a higher stability with the absence of the metastable species.

Since the high binding affinity and aggregation of the two porphyrins prevent the accurate measurement of binding constants by isothermal titration calorimetry (ITC), a single injection experiment was performed in order to determine the binding enthalpy. The Gibbs free energy of the receptor-substrate complexation was estimated directedly from the corresponding fluorescent titrations, providing a value for TAS. Compared with ExBox$^{4+}$, the binding enthalpies of XCage$^{8+}$ are in the range of 7-8 kcal mol$^{-1}$ larger, a major contributing factor to the enhanced affinity. Surface-area overlap analysis reveals[66] that XCage$^{8+}$ provides 1.5 times more binding surface area for the porphyrin core compared with that of ExBox$^{4+}$: 80% of the porphyrin core overlaps with XCage$^{8+}$, whereas only 50% of the porphyrin core overlaps in the case of ExBox$^{4+}$. Compared with Porp-2H, Porp-Zn shows a significant drop in binding enthalpy toward both XCage$^{8+}$ and ExBox$^{4+}$, an observation which agrees well with the titration results which show that the binding of Porp-Zn is generally three times weaker compared with that of Porp-2H. This result implies that the dehydration of the Zn ion upon binding is a high energy demanding process.

Figure 9:
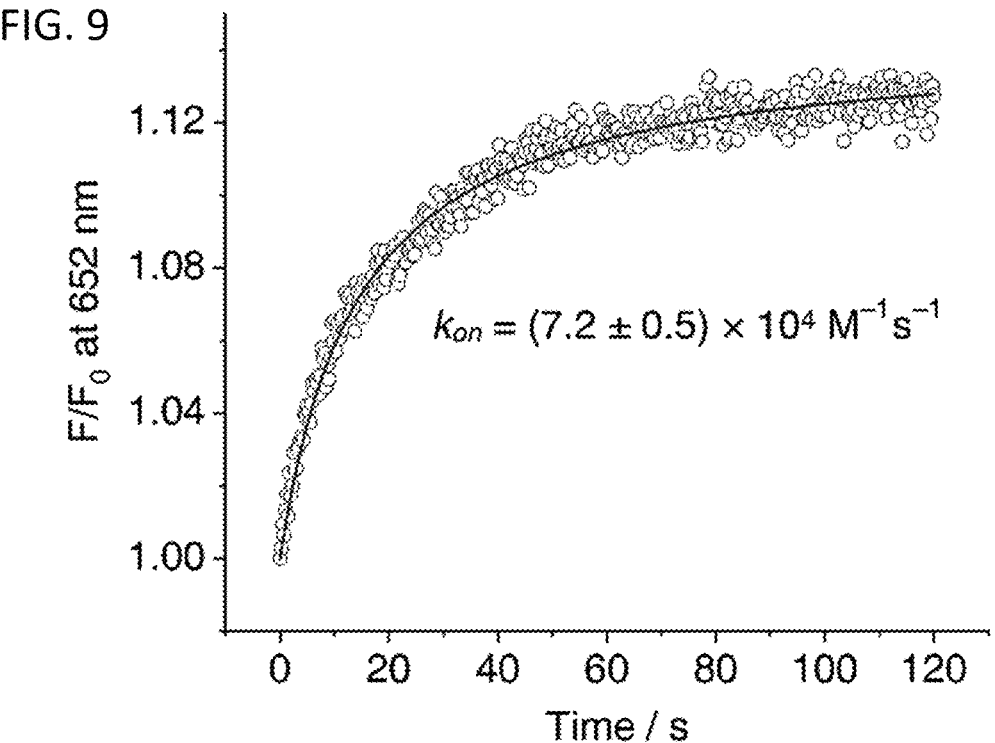
Figure 10:
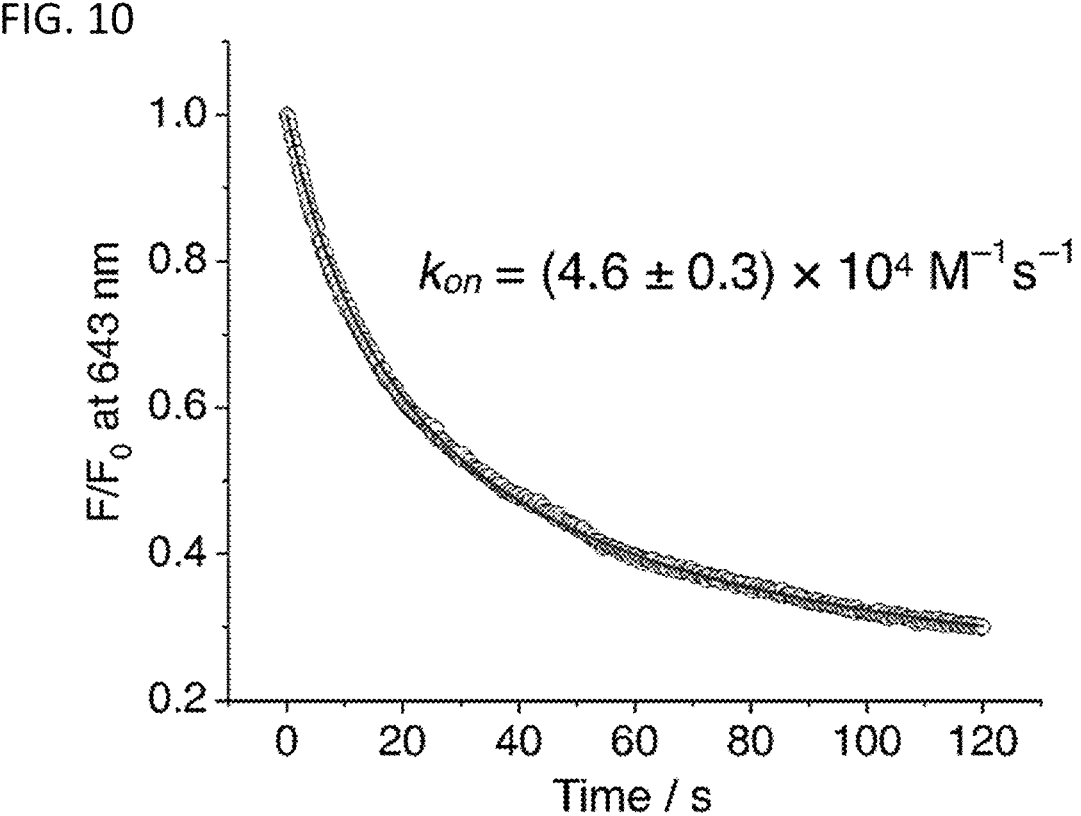

The kinetics of porphyrin encapsulation by XCage$^{8+}$ can be tracked by the change in fluorescence over time. The resulting kinetic profiles were fitted (FIGS. 9 and 10) using a second order kinetics equation. The threading rate constants of XCage$^{8+}$ with Porp-2H and Porp-Zn were determined to be 7.2×$10^4$ and 4.6×$10^4$ M$^{-1}$s$^{-1}$, respectively. The threading of ExBox$^{4+}$ is so rapid that no change of fluorescence over time could be detected following mixing of the tetracationic cyclophane with the porphyrins. The remarkably rapid threading kinetics agrees well with previously reported[24] results where threading a long polymer chain over a macrocyclic receptor is a rapid process. It is necessary to note that the rapid threading kinetics measured here represent the formation of the Porp-2H(Zn)⊂XCage$^{8+}$ complexes, in which co-conformers V and H coexist as a mixture. The transformation of co-conformer V into H is a slow process and requires days to reach completion. Furthermore, the slower threading kinetics of Porp-Zn matches well with the observed co-conformer distribution, where a less amount of the metastable co-conformer V is formed when compared with Porp-2H. The dissociation rate constants ($k_{off}$) for the Porp-2H(Zn)⊂XCage$^{8+}$ complexes can be calculated using the equation $k_{off}=k_{on}/K_a$ and reveals extremely slow dissociation processes with the rate constants and half-lives ($t_{1/2}$) calculated at $4.2 \times 10^{-6}$ ($t_{1/2}$=46 h) and $7.4 \times 10^{-6}$ s$^{-1}$ ($t_{1/2}$=26 h) for Porp-2H⊂XCage$^{8+}$ and Porp-Zn⊂XCage$^{8+}$, respectively. The slow dissociations of Porp-2H(Zn)⊂XCage$^{8+}$ endow the complexes with kinetic stabilities, wherein considerable amounts of the 1:1 complexes can still exist for days, even in the presence of a competitor that has a stronger binding affinity with XCage$^{8+}$.

Chemical Stability

Figure 7:
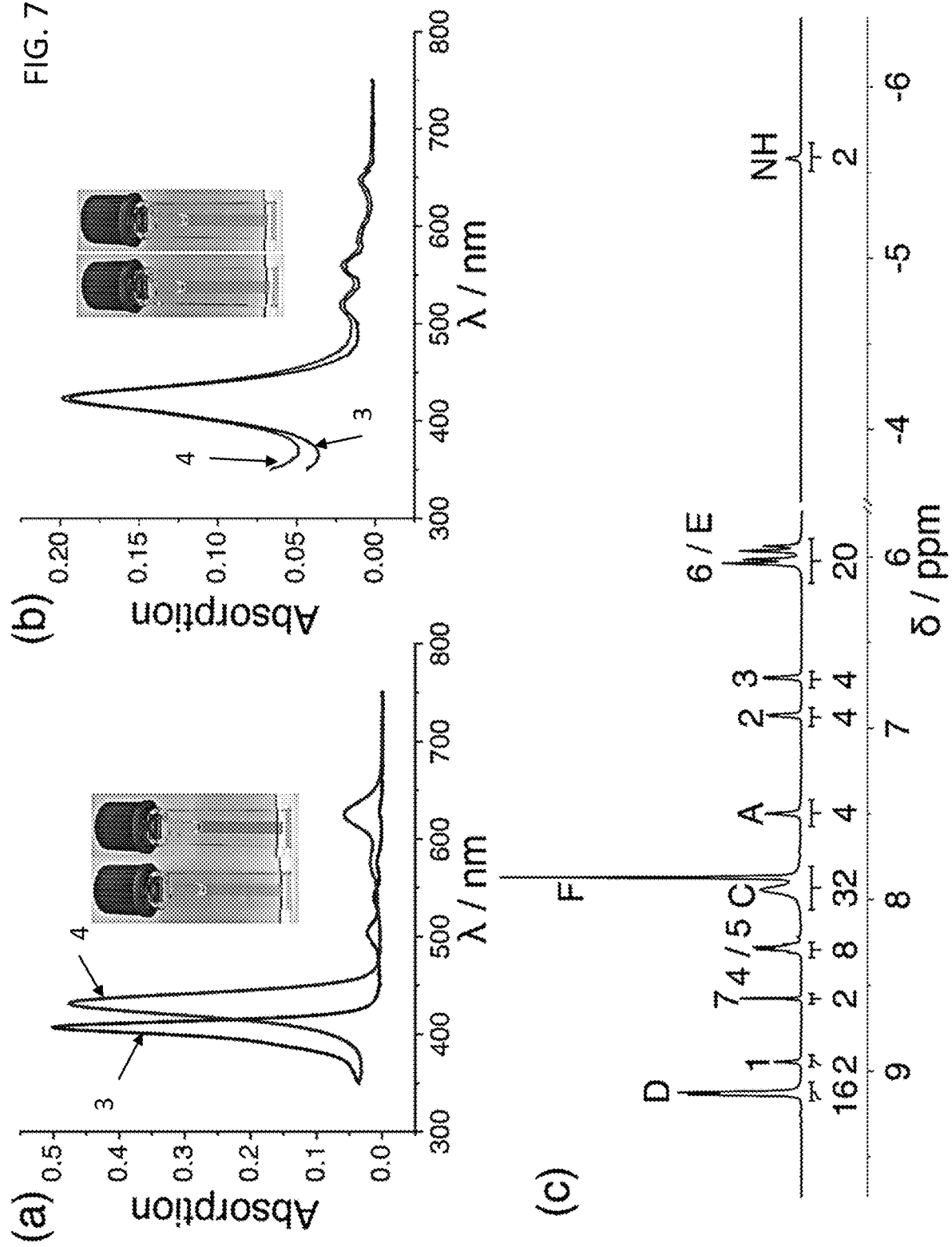
Figure 11:
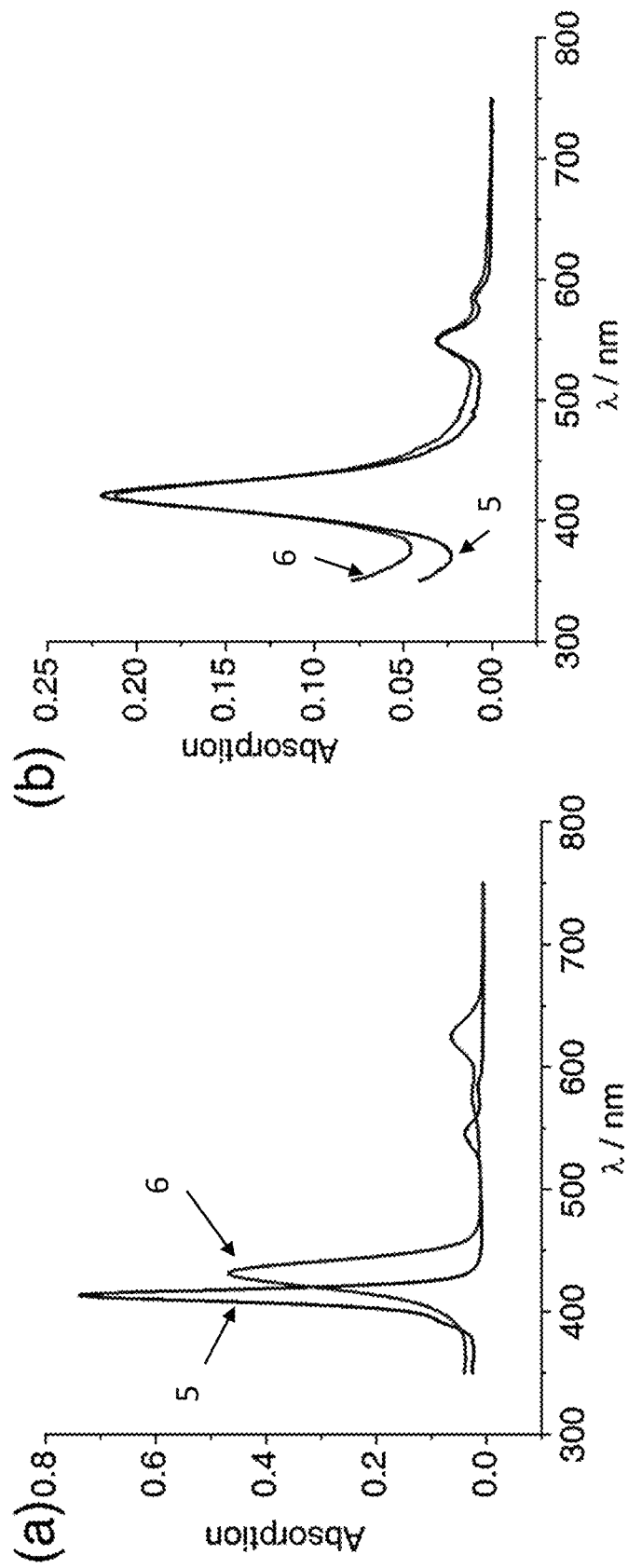
Figure 12:
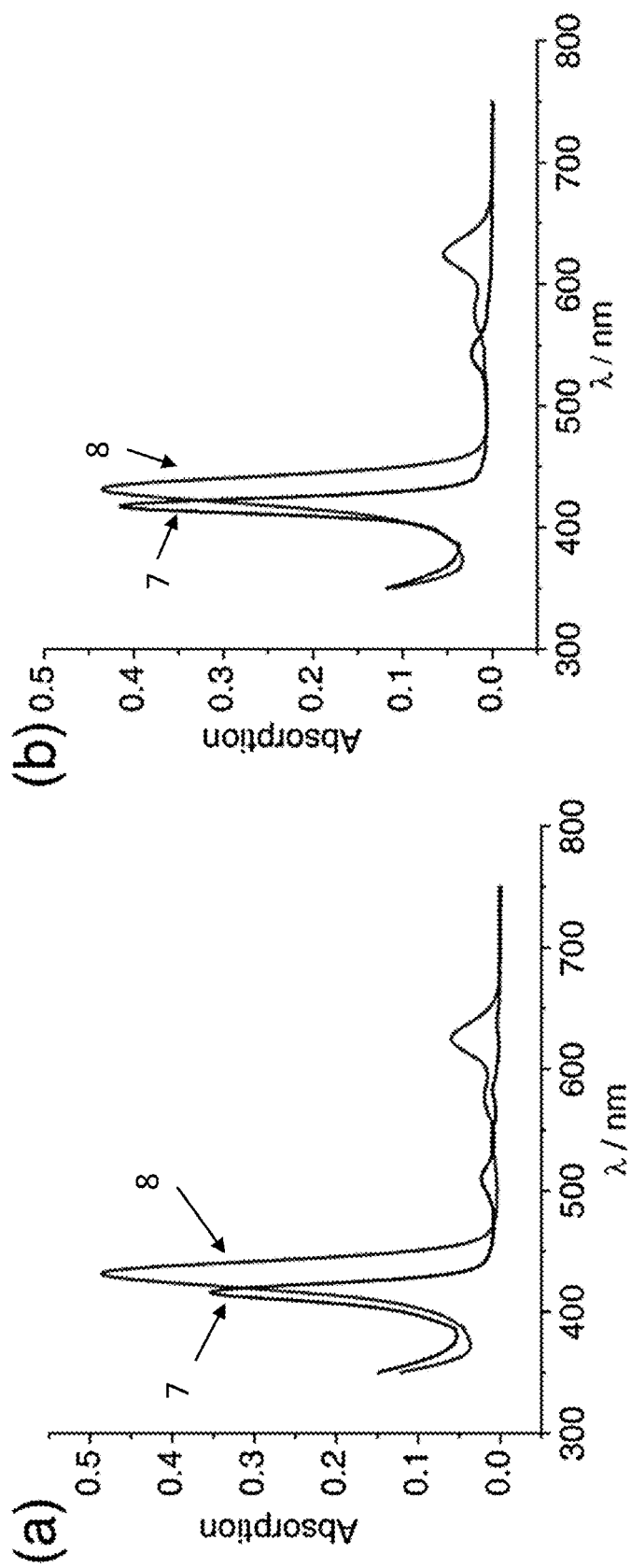

It is well-known that porphyrins and metalloporphyrin are susceptible to acidic environments. Protonation occurs at the pyrrole subunits and leads to changes in photophysical properties, which limit their performance in certain technical scenarios. When added to a solution of HCl (1 M), Porp-2H is protonated instantly, as judged from the change of its color from brown to green and a red-shifted absorption in the UV-Vis spectrum (FIG. 7 panel (a)). In contrast, Porp-2H⊂XCage$^{8+}$ resists protonation and no change is observed (FIG. 7 panel (b)) under the same conditions, i.e., the fact that the high charge density of XCage$^{8+}$ plus its strong affinity with Porp-2H provide protection from H$^+$ attack in aqueous solution. Encapsulation facilitated protonation (positive pKa shifts) is well documented,[68-71] whereas examples of frustrated protonation (negative pKa shifts), induced by synthetic receptors, are rare.[72] There is no example, to our knowledge, where protonation can be totally shut down by molecular encapsulation, a property which would require a high binding affinity and the protection of the protonation site deep inside the binding cavity. As a comparison, the Porp-2H⊂ExBox$^{4+}$ complex with four positive charges and a micromolar binding affinity fails to provide these kinds of protection and instantly decomposes (FIG. 12) into the corresponding protonated species, namely Porp-4 H$^{2+}$ and ExBox$^{4+}$, under the same conditions. On the other hand, Porp-Zn suffers (FIG. 11) from solvolysis in the presence of HCl (1M) as judged by the appearance of Porp-4H$^{2+}$ in its absorption spectrum. Porp-Zn⊂XCage$^{8+}$ remains stable in HCl solution.

Considering the excellent performance of XCage$^{8+}$ that prevents H$^+$ from attacking the porphyrin core, we envisioned that D/H exchanges, involving the pyrrole subunits in deuterated solvents, should also be blocked. In order to test this hypothesis, Porp-2H⊂XCage$^{8+}$ was prepared, first of all in H$_2$O, and subsequently re-dissolved in D$_2$O. The $^1$H NMR spectrum of Porp-2H⊂XCage$^{8+}$ shows (FIG. 7 panel (c)) clearly NH signals at −5.6 ppm, resulting from the shielding effect provided by both the porphyrin core and the biphenyl units in XCage$^{8+}$. A comparison of the NH integration, with respect to other porphyrin proton signals, indicates[73] no sign of D/H exchange.

Conclusions

The tricyclic cyclophane serves as an excellent receptor for both the free-base and Zn-porphyrins with subnanomolar affinity in water. The tricyclic nature of XCage$^{8+}$ permits the formation of two co-conformationally isomeric complexes with both porphyrins, as revealed by $^1$H NMR spectroscopy. XCage$^{8+}$ is able to modulate both the photophysical properties and chemical reactivities of the encapsulated porphyrins. The isolation of both porphyrins by XCage$^{8+}$ with ultrahigh stabilities provides us with a new platform to investigate porphyrins at the single-molecule level.[74-76] The encapsulation characterizing the Porp-Zn⊂XCage$^{8+}$ complex allows for a library of metalloporphyrins with a wide range of properties, leading to applications in nanotechnology,[43,77] artificial photodevice fabracation[78,79] and biomedical science.[41,80]

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

EXAMPLES

General Information

Commercially available solvents and chemicals were purchased from Sigma-Aldrich and Fisher Scientific and used without further purification unless otherwise stated. Di(1H-pyrrol-2-yl)methane was purchased from Ambeed. Compounds XCage.8CF3CO$_2$,[S1] ExBox.4Cl,[S2] mPorp-2H[S3] and mPorp-Zn[S4] were prepared using previously reported procedures. Water was deionized, and micro filtered using Milli-Q water filtration station. Thin layer chromatography (TLC) was performed on silica gel 60 F254 (E. Merck). Preparative thin layer chromatography was conducted using Analtech PO2013 silica gel uniplate (thickness: 1000 μm). Flash column chromatography was carried out by Combiflash Rf 200 purification system. Reversed phase column chromatography was performed on Combiflash NEXTGEN 300+ system with SNAP ULTRA C18 cartridges, which were purchased from Biotage. UV-Vis Absorption spectra were recorded in a glass cuvette using a UV-3600 Shimadzu spectrophotometer. Steady-state emission spectra were acquired in a quartz cuvette with an optical path-length of 10 mm containing the solution of interest using HORIBA Fluoromax4 spectrofluorometer, which was equipped with an integrating sphere for absolute photoluminescence quantum yield determination. Nuclear magnetic resonance (NMR) spectra were recorded on Bruker AVANCE III 500 MHz spectrometer equipped with DCH CryoProbe, with working frequencies of 500 MHz for $^1$H and 125 MHz for $^{13}$C nuclei. Chemical shifts are reported in ppm relative to the signals corresponding to the residual non-deuterated solvents (CDCl$_3$: δ=7.26 ppm; CD$_3$OD: δ=4.74 ppm; D$_2$O: δ=4.74 ppm). High-resolution mass spectra were measured on an Agilent 6210 Time of Flight (TOF) LC-MS, using an ESI source, coupled with Agilent 1100 HPLC stack, using direct infusion (0.6 mL/min). MALDI-TOF mass spectra were measured on a Bruker AutoFlex-III under high resolution reflection mode; 2,5-dihydroxybenzoic acid was used as the matrix. Single crystal data were obtained on a Bruker Kappa APEX2 CCD diffractometer using Cu-Kα radiation. Isothermal titration was performed by TA Nano Isothermal Titration Calorimeter. Detailed experimental procedures are provided below in the appropriate sections of this supplementary information.

Synthetic Protocols

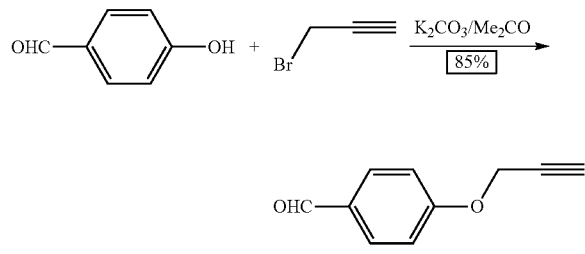

Scheme 1. Synthesis of 4-(prop-2-yn-1-yloxy)benzaldehyde 4-(Prop-2-yn-1-yloxy)benzaldehyde: 4-Hydroxylbenzaldyhyde (5.0 g 41 mmol), K$_2$CO$_3$ (11.3 g, 82 mmol) and propargyl bromide (7.3 g, 61 mmol) were suspended in Me$_2$CO (150 mL), and the reaction mixture was stirred at 65° C. overnight. After cooling to room temperature, the solvent was removed by vacuum. EtOAc (350 mL) was added to the residue, which was subsequently washed with H$_2$O (100×3) and brine (100 mL). After drying (Na$_2$SO$_4$), the solvent was removed and the residue was recrystallized from EtOH to afford the product as an off-white solid (5.6 g, 85% yield). $^1$H NMR (500 MHz, CDCl$_3$) δ 9.89 (s, 1H), 7.91-7.78 (m, 2H), 7.13-7.01 (m, 2H), 4.77 (d, J=2.4 Hz, 2H), 2.55 (t, J=2.4 Hz, 1H).

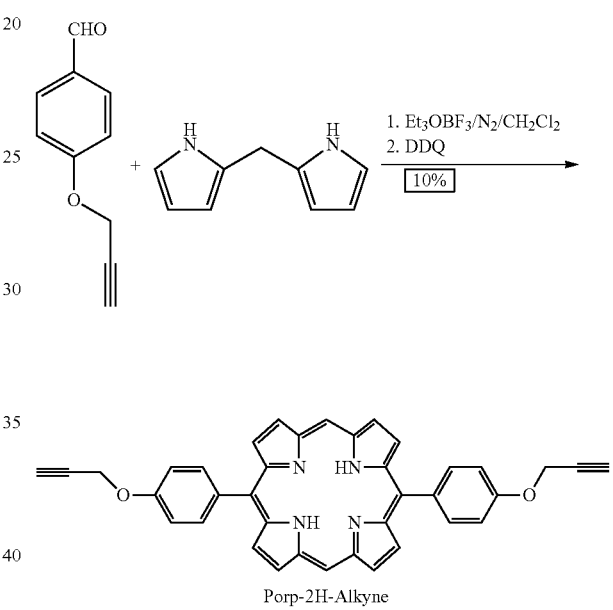

Scheme 2. Synthesis of Porp-2H-Alkyne

Porp-2H-Alkyne: 4-(Prop-2-yn-1-yloxy)benzaldehyde (329 mg, 2.1 mmol) and di(1H-pyrrol-2-yl)methane (300 mg, 2.1 mmol) were dissolved in CH$_2$Cl$_2$ (100 mL). The resulting solution was degassed by bubbling N$_2$ gas for 10 min, then Et$_3$OBF$_3$ (30 mg, 0.16 mmol) was added. Under N$_2$ protection, the reaction mixture was stirred at room temperature for 4 h, after which DDQ (568 mg, 2.5 mmol) was added. The reaction mixture was stirred at room temperature for 1 h. The solvent was removed, and the residue was washed by MeOH. The remaining black solid was extracted with CHCl$_3$ (300 mL×3). After drying (Na$_2$SO$_4$), the solvent was removed to afford the product as a purple solid (58 mg, 10% yield). $^1$H NMR (500 MHz, CDCl$_3$) δ 10.29 (s, 2H), 9.38 (d, J=4.5 Hz, 4H), 9.09 (d, J=4.5 Hz, 4H), 8.19 (d, J=8.3 Hz, 4H), 7.41 (d, J=8.4 Hz, 4H), 5.00 (d, J=2.4 Hz, 4H), 2.70 (s, 2H), −3.10 (s, 2H). Poor solubility of Porp-2H-Alkyne prevented $^{13}$C analysis. HRMS-ESI (m/z) for Porp-2H-Alkyne: Calcd for C$_{38}$H$_{27}$N$_4$O$_2^+$: m/z=571.2129 [M+H]$^+$; found 571.2141 [M+H]$^+$.

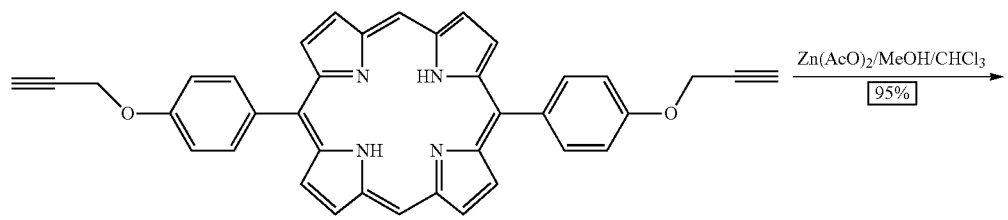

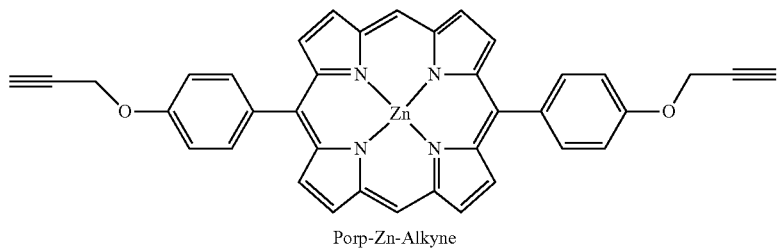

Porp-Zn-Alkyne

Scheme 3. Synthesis of Porp-Zn-Alkyne

Porp-Zn-Alkyne: A solution of Porp-Zn-Alkyne (50 mg, 0.088 mmol) in CHCl$_3$ (30 mL) was mixed with a solution of Zn(AcO)$_2$·2H$_2$O (180 mg, 0.62 mmol) in MeOH (2 mL). The reaction mixture was stirred at room temperature overnight. CHCl$_3$ (200 mL) was added to the reaction mixture, which was washed with H$_2$O (100 mL×3) and brine (100 mL). After drying (Na$_2$SO$_4$), the solvent was removed to afford the product as a red solid (53 mg, 95% yield). $^1$H NMR (500 MHz, CDCl$_3$) δ 10.32 (s, 2H), 9.44 (d, J=4.5 Hz, 41H), 9.16 (d, J=4.4 Hz, 4H), 8.22-8.12 (m, 4H), 7.44-7.36 (m, 4H), 5.01 (d, J=2.4 Hz, 4H), 2.72 (t, J=2.4 Hz, 2H). Poor solubility of Porp-Zn-Alkyne prevented $^{13}$C analysis. HRMS-ESI (m/z) for Porp-Zn-Alkyne: Calcd for C$_{38}$H$_{24}$N$_4$O$_2$Zn$^+$: m/z=632.1191 [M]$^+$; found 632.1191 [M]$^+$.

Scheme 4. Synthesis of Porp-Zn

Porp-Zn: Porp-Zn-Alkyne (15 mg, 0.023 mmol), mPEG$_{2000}$-N$_3$ (100 mg, 0.0488 mmol), TBTACu(I)Br (2 mg, 0.003 mmol) and Et$_3$N (2 drops) were suspended in CHCl$_3$ (5 mL). The reaction mixture was stirred at 40° C. overnight. After removing the solvent, the residue was purified by preparative TLC using THF (10%)/MeOH (10%)/CH$_2$Cl$_2$ (80%) to obtain the product as a dark red solid (73 mg, 71% yield). $^1$H NMR (500 MHz, CDCl$_3$) δ 10.26 (s, 2H), 9.40 (d, J=4.5 Hz, 4H), 9.12 (d, J=4.3 Hz, 4H), 8.14 (d, J=8.2 Hz, 4H), 7.83 (s, 2H), 7.31 (d, J=8.0 Hz, 4H), 4.99 (s, 4H), 4.47 (s, 4H), 3.82 (t, J=5.0 Hz, 4H), 3.67-3.25 (m, 386H). MS-MAL-DI (m/z) for Porp-Zn: clustered peaks found around 4571.

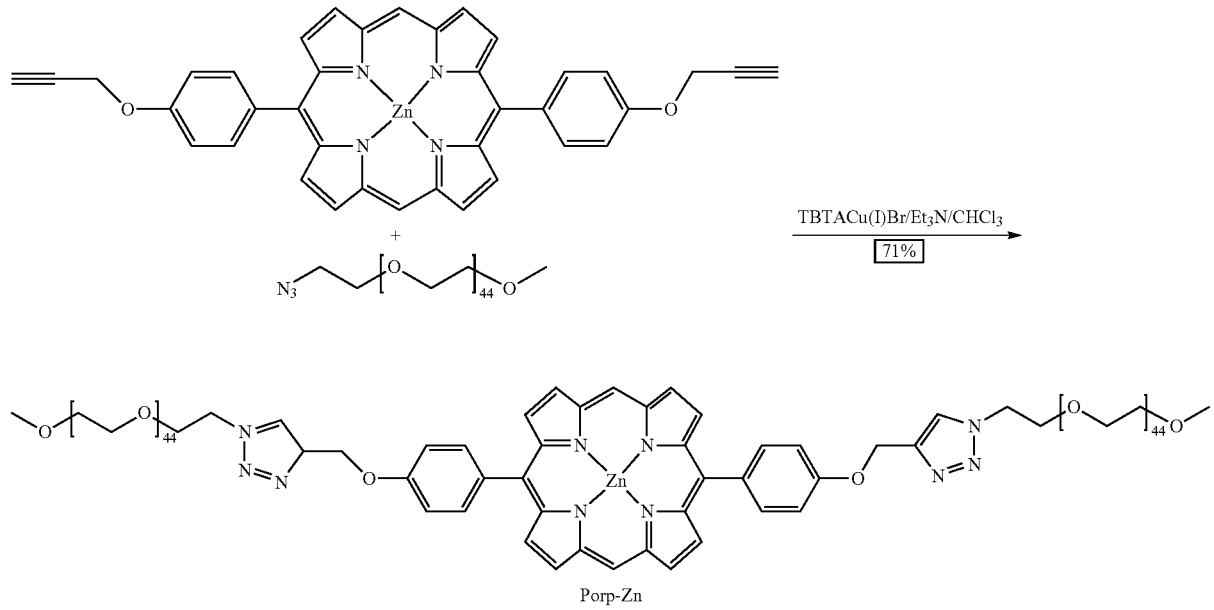

Porp-Zn

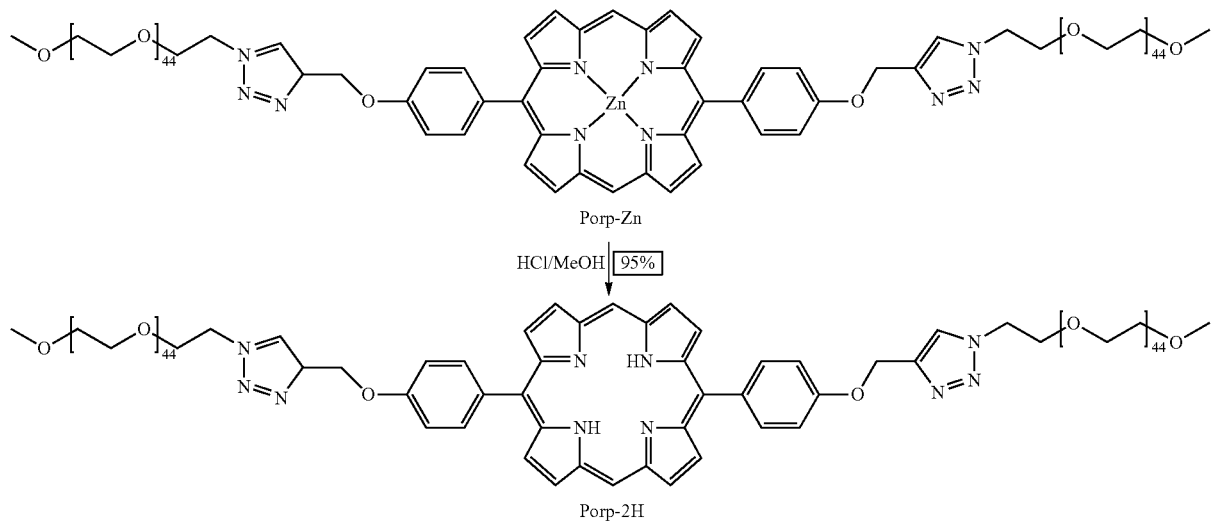

Scheme 5. Synthesis of Porp-2H

Porp-2H: Porp-Zn (65 mg, 0.014 mmol) was dissolved in MeOH (10 mL), and HCl (12 M, 1 mL) was added dropwise to the solution. The reaction mixture was stirred at room temperature for 10 min. The complete of the reaction was confirmed by checking the fluorescence emission spectra of the reaction mixture to the point where no fluorescence emission of Porp-Zn could be detected. $CH_2Cl_2$ (100 mL) was added to the reaction mixture, and the resulting solution was washed with NaOH (1M, 100 mL×3) until the color of the solution changed from green to dark red. After drying ($Na_2SO_4$), the solvent was removed to obtain the product as a dark red solid (60 mg, 95% yield). $^1$H NMR (500 MHz, $CDCl_3$) δ 10.29 (s, 2H), 9.38 (d, J=4.6 Hz, 4H), 9.08 (d, J=4.5 Hz, 4H), 8.23-8.15 (m, 4H), 8.06 (s, 2H), 7.48-7.41 (m, 4H), 5.52 (s, 4H), 4.66 (t, J=5.0 Hz, 4H), 3.97 (t, J=5.1 Hz, 4H), 3.75-3.43 (m, 354H), 3.36 (s, 6H), −3.10 (s, 2H). MS-MALDI (m/z) for Porp-21: clustered peaks found around 4552.

Crystallographic Analysis (1) Crystal Structure of mPorp-2H.XCage-8PF$_6$ (a) Method: XCage.8CF$_3$CO$_2$ (2.2 mg, 1 mmol) and mPorp-2H (0.9 mg, 2 mmol) was dissolved in DMF (1 mL), and the resulting solution was heated at 80° C. for 30 min. DMF was then removed by vacuum, and the residue was dissolved in $H_2O$. The solution was filtrated through a 0.45 μm PTFE filter to remove insoluble mPorp-2H. NH$_4$PF$_6$ was added, and the precipitation was collected by centrifuge to obtain mPorp-2H ⊂ XCage.8PF$_6$ as a red solid, which was subsequently dissolved in Me$_2$CO (1 mL). Slow vapor diffusion of iPr$_2$O ether into an Me$_2$CO solution mPorp-2H ⊂ XCage-8PF& for 3 days yielded dark red colored crystals of mPorp-2H ⊂ XCage.8PF$_6$. A suitable crystal was selected, and the crystal was mounted on a MITIGEN holder on a Bruker APEX-II CCD diffractometer. The crystal was kept at 100.0 K during data collection. Using Olex2,[S5] the structure was solved with the ShelXT[S6] structure solution program using Dual Space and refined with the XL[S7] refinement package using least squares minimization.

(b) Crystal Parameters: Empirical formula=$C_{134}H_{110}F_{48}N_{12}O_2P_8$, formula weight=3080.09, triclinic, space group P-1 (no. 2), a=14.66878(16), b=17.5021(2), c=19.14358(19) Å, α=108.9696(10), β=106.6927(10), γ=102.2968(10)°, V=4189.71(8) Å$^3$, z=1, T=100.01(10) K, μ(CuKα)=1.665 mm$^{-1}$, D$_{calc}$=1.221 g/mm$^3$, 60466 reflections measured (5.292≤2Θ≤154.218), 17224 unique (R$_{int}$=0.0648, R$_{sigma}$=0.0562) which were used in all calculations. The final R$_1$ was 0.0571 (I>2σ(I)) and wR$_2$ was 0.1671 (all data).

(c) Refinement Details: Distance restraints were imposed on the disordered PF$_6$ anions. The enhanced rigid-bond restraint (SHELX keyword RIGU) was applied on the disordered PF, anions.

(d) Solvent Treatment Details: The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell =1215.7 Å$^3$ [29.0%] Total electron count/cell=327.5.

(2) Crystal Structure of mPorp-Zn ⊂ XCage.8PF$_6$ (a) Method: XCage.8CF3CO2 (2.2 mg, 1 mmol) and mPorp-Zn (0.9 mg, 2 mmol) were dissolved in DMF (1 mL), and the resulting solution was heated at 80° C. for 30 min. DMF was then removed by vacuum, and the residue was dissolved in 120. The solution was filtrated through a 0.45 μm PTFE filter to remove insoluble mPorp-Zn. NH$_4$PF$_6$ was added, and the precipitation was collected by centrifuge to obtain mPorp-Zn ⊂ XCage8PF$_6$ as a red solid, which was subsequently dissolved in Me$_2$CO (1 mL). Slow vapor diffusion of iPr$_2$O into an Me$_2$CO solution mPorp-Zn ⊂ XCage.8PF$_6$ for three days yielded dark red colored crystals of mPorp-Zn ⊂ XCage.8PF$_6$. A suitable crystal was selected, and the crystal was mounted on a MITIGEN holder on a Bruker APEX-II CCD diffractometer. The crystal was kept at 100.0 K during data collection. Using Olex2,[S5] the structure was solved with the ShelXT[S6] structure solution program using Dual Space and refined with the XL[S7] refinement package using least squares minimization.

(b) Crystal Parameters: Empirical formula=$C_{140}H_{120}F_{48}N_{12}O_4P_8Zn$, formula weight=3259.60, triclinic, space group P-1 (no. 2), a=14.6658(16), b=17.540(2), c:=19.0390(19) Å, α=108.894 (8), β=106.654(8), γ=102.130(8)°, V=4184.0(9) Å$^3$, Z=1, T=298.97 K, μ(CuKα) 1.845 mm$^{-1}$, D$_{calc}$=1.294 g/mm$^3$, 18658 reflections measured (5.312≤2Θ≤118.768), 11339 unique ($R_{int}$=0.0678, $R_{sigma}$=0.1044) which were used in all calculations. The final $R_1$ was 0.0928 (I>2σ(I)) and w$R_2$ was 0.2863 (all data).

(c) Refinement Details: Distance restraints were imposed on the disordered $PF_6^-$ anion. The enhanced rigid-bond restraint (SHELX keyword RIGU) was also imposed on the disordered $PF_6^-$ anion.[S8]

(d) Solvent Treatment Details: The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=0.1034.0 Å$^3$ [24.7%] Total electron count/cell=275.8.

Structure Optimization

The initial structural coordinates for co-conformers V were created based on the single crystal structures of mPorp-2H ⊂ XCage$^{8+}$ and mPorp-Zn c XCage. The structures were optimized using semi-empirical method at PM6-D3H4 level using MOPAC2016 program.[S9]

Independent Gradient Model Analysis

Independent gradient model (IGM) analysis is an approach[S10] based on pro-molecular density to identify and isolate intermolecular interactions. Strong polar attractions and van der Waals contacts are visualized as an iso-surface with blue and green color respectively. Single crystal structures of the receptor-substrate complexes were used as input file. The binding surface was calculated by Multiwfn 3.6 program[S11] through function 20 (visual study of weak interaction) and visualized by Chimera program.[S12]

Surface-Area Overlap (SAO) Analysis

Surface-area overlap analysis was performed by Chimera and ImageJ software. Single crystal structures were truncated by removing the top half of XCage$^{8+}$ or ExBox$^{4+}$ and visualized by Chimera.[S13] Porphyrins, XCage$^{8+}$, and ExBox$^{4+}$ were colored to show the bridging units (yellow), the binding cavity of the receptor (light sea green), the area of substrate (magenta), and the overlapping portion between the receptor and substrate (purple). ImageJ 1.49 software was used to measure the percent of SAO in each receptor-substrate complex. Values were calculated for the SAO-receptor (the overlapping portion between the receptor and substrate divided by the total area of the receptor) and SAO-substrate (the overlapping portion between the receptor and substrate divided by the total area of the substrate).

TD-DFT Calculation

Single crystal structure of Porp-21H ⊂ XCage$^{8+}$ and Porp-Zn ⊂ XCage$^{8+}$ was used as initial input coordinates, and the structures were optimized by Gaussian 16 program at B3LYP/6-31G* level for C, H, and N atoms; the Zn atom was optimized at LANL2DZ level. The frontier orbitals and UV-absorption spectra were calculated by TD-DFT calculations at the same level.

Transient State Absorption Measurements

Femtosecond transient absorption spectroscopy (fsTA) experiments were performed on a Ti:sapphire laser system described in detail previously.[S10] Pump pulses at 414 nm (1 μJ/pulse) were generated by frequency-doubled of the 827 nm fundamental. A femtosecond excitation beam (TOPAS-White, Light-Conversion, Ltd) was used to generate 330 nm pump pulses (0.7-1.6 μJ/pulse). Nanosecond transient absorption spectroscopy (nsTA) experiments were performed using a commercial spectrometer (EOS, Ultrafast Systems) with the same excitation beams as the fsTA experiments. 1 mm cuvettes were used to carry solution samples. The samples were bubbled with $N_2$ for 20 min before the nsTA measurements. All the measurements were carried out at room temperature. Details of kinetic fittings were described[S14] in a previously published paper.

Association Studies by Fluorescence and Isothermal Titration Calorimetry

In the experiments shown below, all of the solutions were prepared in spectroscopic grade solvents and equilibrated for 24 h at room temperature before use. All of the studies were independently duplicated, and the corresponding isotherm fittings were used to calculate the average $K_a$ or $k_{on}$ with the standard error.

Direct fluorescence titration experiments: The binding of ExBox$^{4+}$ with Porp-2H or Porp-Zn in water induces the fluorescence quenching of the corresponding porphyrins, which was utilized as the signals to track the formation of inclusion complexes. In general, the stock solution of ExBox$^{4+}$ (500 μM) was injected in aliquots into the solution of Porp-2H or Porp-Zn (5-10 μM). The fluorescence quenching was recorded until no further changed observed upon adding ExBox$^{4+}$. The resulting isotherm was fitted by a 1:1 binding model[S15] to calculate the binding constant $K_a$ using Origin Lab 8.6 software.[S16]

Displacement fluorescence titration experiments: The displacement of porphyrins from Porp-2H ⊂ ExBox$^{4+}$ or Porp-Zn ⊂ ExBox$^{4+}$ by XCage$^{8+}$ to form Porp-2H ⊂ XCage$^{8+}$ or Porp-Zn ⊂ XCage$^{8+}$ regenerates the fluorescence emission of porphyrin, and the turn-on fluorescence was monitored as the signals to track the formation of the porphyrin inclusion complexes with XCage$^{8+}$. The displacement process is too slow to perform direct titration experiments, we chose to perform the titration experiments by preparing separate samples with varied molar ratio of XCage$^{8+}$ to Porphyrins. In general, three sets of 16 samples of Porp-2H c ExBox$^{4+}$ or Porp-Zn ⊂ ExBox$^{4+}$ (porphyrin: 5-10 μM, ExBox$^{4+}$: 100 μM) were prepared with varied molar ratio of XCage$^{8+}$ to porphyrins (0-2.5 molar equivalent). The samples were equilibrated at room temperature for 6 h, and the fluorescence intensity of each sample was recorded. The average fluorescence intensity of the three sets samples was plotted against the concentration of XCage$^{8+}$ to generate the binding isotherm, which was fitted by a displacement binding model[S15] to calculate the binding constant $K_a$ using Origin Lab 8.6 software[S16].

Binding kinetics studies: The binding kinetics were studied by recording the change of fluorescence overtime after mixing equal molar of XCage$^{8+}$ and porphyrins. The resulting kinetic was fitted[S17] according to the second order kinetics model. The threading kinetics between ExBox$^1$ and porphyrins are too rapid to be monitored.

Isothermal titration calorimetry: Isothermal titration was performed by TA Nano Isothermal Titration Calorimeter at 25° C. A Hastelloy cell was used with an active cell volume 190 μL. The stirring speed was set at 150 rpm. The solutions of receptors and substrates were prepared in Milli-Q water and allowed to equilibrate overnight if necessary. The aggregation of porphyrins and their high affinity binding prevented the accurate determination of binding constants, we thus only evaluated the binding enthalpy by single injection method.[S17]

D/H Exchange Monitored by NMR Spectroscopy

Porp-2H ⊂ XCage$^{8+}$ was firstly prepared in $H_2O$ by mixing equal concentration of XCage$^{8+}$ (2 mM) and Porp-2H (2 mM) at 80° C. for 48 h. After removing solvent, the resulting TFA salt of Porp-2H ⊂ XCage$^{8+}$ was dissolved in $D_2O$ and the $^1H$ NMR spectrum was collected. As a control, the $^1H$ NMR spectrum of Porp-2H in $D_2O$ is broad on account of its aggregation, only PEG signal is observed. Consequently, $^1$H NMR spectrum of Porp-2H was collected in CD$_3$OD, where the NH signals are exchanged to ND.

TABLES

TABLE 1

Binding Constants and Thermodynamic Data at 25° C.[a]

| entry | Host | Guest | $K_a$[b]/M$^{-1}$ | $\Delta G$[c]/ kcal mol$^{-1}$ | $\Delta H$[d]/ kcal mol$^{-1}$ | $T\Delta S$/ kcal mol$^{-1}$ |
|---|---|---|---|---|---|---|
| 1 | ExBox$^{4+}$ | Porp-2H | 1.4 × 10$^7$ | −9.7 | −7.7 | +2.0 |
| 2 | ExBox$^{4+}$ | Porp-Zn | 5.1 × 10$^6$ | −9.1 | −5.4 | +3.7 |
| 3 | XCage$^{8+}$ | Porp-2H | 1.7 × 10$^{10}$ | −13.9 | −16.1 | −2.2 |
| 4 | XCage$^{8+}$ | Porp-Zn | 6.2 × 10$^9$ | −13.4 | −12.8 | +0.6 |

[a]The standard errors are presented in Supporting Information.
[b] Determined by fluorescence titration.
[c] Estimated from fluorescence titration.
[d]Measured by ITC

TABLE 2

Summary of Photophysical Properties of Porp-2H and Porp-2H ⊂ XCage$^{8+}$ in H$_2$O

| Compound | Porp-2H | Porp-2H ⊂ XCage$^{8+}$ |
|---|---|---|
| $\lambda_{abs}$ (nm) | 406/508/542/572/632 | 422/518/560/592/648 |
| $\lambda_{ex}$ (nm) | 385/418/504/540/576/631 | 323/502/519/560/589/647 |
| $\lambda_{em}$ (nm) | 634/696 | 652/719 |
| logε (Soret peak) | 5.4 | 5.0 |
| $\Phi_f$[a] | 0.16 | 0.25 |

[a]Quantum yields were measured using an integration sphere (ex: 440-550 nm, em: 550-800 nm) at 1 µM sample concentration.

TABLE 3

Summary of Photophysical Properties of Porp-Zn and Porp-Zn ⊂ XCage$^{8+}$ in H$_2$O

| Compound | Porp-Zn | Porp-Zn ⊂ XCage$^{8+}$ |
|---|---|---|
| $\lambda_{abs}$ (nm) | 413/547/585 | 421/550/585 |
| $\lambda_{ex}$ (nm) | 397/427/548/585 | 321/415/548/584 |
| $\lambda_{em}$ (nm) | 594/643 | 596/645 |
| logε (Soret peak) | 5.8 | 5.1 |
| $\Phi_f$[a] | 0.05 | 0.006 |

[a]Quantum yields were measured using an integration sphere (ex: 414-460 nm, em: 460-800 nm) at 1 µM sample concentration.

REFERENCE (1) Persch, E.; Dumele, O.; Diederich, F. Molecular Recognition in Chemical and Biological Systems. *Angew. Chem. Int. Ed.* 2015, 54, 3290-3327.

(2) Houk, K. N.; Leach, A. G.; Kim, S. P.; Zhang, X. Binding Affinities of Host-Guest, Protein-Ligand, and Protein-Transition-State Complexes. *Angew. Chem. Int. Ed.* 2003, 42, 4872-4897.

(3) *Synthetic Receptors for Biomolecules: Design Principles and Applications*, First Edition; Smith, B. D., Ed.; Royal Society of Chemistry, 2015.

(4) Liu, W.; Samanta, S. K.; Smith, B. D.; Isaacs, L. Synthetic Mimics of Biotin/(Strept)Avidin. *Chem. Soc. Rev.* 2017, 46, 2391-2403.

(5) Cao, L.; Šekutor, M.; Zavalij, P. Y.; Mlinarić-Majerski, K.; Glaser, R.; Isaacs, L. Cucurbit[7]uril.Guest Pair with an Attomolar Dissociation Constant. *Angew. Chem. Int. Ed.* 2014, 53, 988-993.

(6) Tromans, R. A.; Carter, T. S.; Chabanne, L.; Crump, M. P.; Li, H.; Matlock, J. V.; Orchard, M. G.; Davis, A. P. A Biomimetic Receptor for Glucose. *Nat. Chem.* 2019, 1/, 52-56.

(7) Shetty, D.; Khedkar, J. K.; Park, K. M.; Kim, K. Can We Beat the Biotin-Avidin Pair?: Cucurbit[7]uril-Based Ultrahigh Affinity Host-Guest Complexes and Their Applications. *Chem. Soc. Rev.* 2015, 44, 8747-8761.

(8) Mako, T. L.; Racicot, J. M.; Levine, M. Supramolecular Luminescent Sensors. Chem. Rev. 2019, 119, 322-477.

(9) Jia, F.; Hupatz, H.; Yang, L. P.; Schröder, H. V.; Li, D. H.; Xin, S.; Lentz, D.; Witte, F.; Xie, X.; Paulus, B.; Schalley, C. A.; Jiang, W. Naphthocage: A Flexible yet Extremely Strong Binder for Singly Charged Organic Cations. *J. Am. Chem. Soc.* 2019, 141, 4468-4473.

(10) Cheng, C.; McGonigal, P. R.; Schneebeli, S. T.; Li, H.; Vermeulen, N. A.; Ke, C.; Stoddart, J. F. An Artificial Molecular Pump. *Nat. Nanotechnol.* 2015, 10, 547-553.

(11) Qiu, Y.; Zhang, L.; Pezzato, C.; Feng, Y.; Li, W.; Nguyen, M. T.; Cheng, C.; Shen, D.; Guo, Q. H.; Shi, Y.; Cai, K.; Alsubaie, F. M.; Astumian, R. D.; Stoddart, J. F. A Molecular Dual Pump. *J. Am. Chem. Voc.* 2019, 141, 17472-17476.

(12) Yoshizawa, M.; Catti, L. Bent Anthracene Dimers as Versatile Building Blocks for Supramolecular Capsules. *Acc. Chem. Res.* 2019, 52, 2392-2404.

(13) Yazaki, K.; Catti, L.; Yoshizawa, M. Polyaromatic Molecular Tubes: From Strategic Synthesis to Host Functions. *Chem. Commun.* 2018, 54, 3195-3206.

(14) Yang, L. P.; Wang, X.; Yao, H.; Jiang, W. Naphthotubes: Macrocyclic Hosts with a Biomimetic Cavity Feature. *Acc. Chem. Res.* 2019, 53, 198-208.

(15) Ke, H.; Yang, L.-P.; Xie, M.; Chen, Z.; Yao, H.; Jiang, W. Shear-induced Assembly of a Transient yet Highly Stretchable Hydrogel Based on Pseudopolyrotaxanes. *Nat. Chem.* 2019, 11, 470-477.

(16) Yamashina, M.; Sartin, M. M.; Sei, Y.; Akita, M.; Takeuchi, S.; Tahara, T.; Yoshizawa, M. Preparation of Highly Fluorescent Host-Guest Complexes with Tunable Color Upon Encapsulation. *J. Am. Chem. Soc.* 2015, 137, 9266-9269.

(17) Hagiwara, K.; Akita, M.; Yoshizawa, M. An Aqueous Molecular Tube with Polyaromatic Frameworks Capable of Binding Fluorescent Dyes. *Chem. Sci.* 2015, 6, 259-263.

(18) Kondo, K.; Akita, M.; Yoshizawa, M. Solubility Switching of Metallophthalocyanines and Their Larger Derivatives upon Encapsulation. *Chem. Eur.* 2016, 22, 1937-1940.

(19) Tsutsui, T.; Kusaba, S.; Yamashina, M.; Akita, M.; Yoshizawa, M. Open Versus Closed Polyaromatic Nanocavity: Enhanced Host Abilities toward Large Dyes and Pigments. *Chem. Eur. J.* 2019, 25, 4320-4324.

(20) Arunkumar, E.; Forbes, C. C.; Smith, B. D. Improving the Properties of Organic Dyes by Molecular Encapsulation. *Eur. J. Org. Chem.* 2005, 19, 4051-4059.

(21) Koner, A. L.; Nan, W. M. Cucurbituril Encapsulation of Fluorescent Dyes. *Supramol. Chem.* 2007, 19, 55-66.

(22) Dsouza, R. N.; Pischel, U.; Nau, W. M. Fluorescent Dyes and Their Supramolecular Host/Guest Complexes with Macrocycles in Aqueous Solution. *Chem. Rev.* 2011, 11, 7941-7980.

(23) Liu, W.; Johnson, A.; Smith, B. D. Guest Back-Folding: A Molecular Design Strategy That Produces a Deep-Red Fluorescent Host/Guest Pair with Picomolar Affinity in Water. *J. Am. Chem. Soc.* 2018, 140, 3361-3370.

(24) Peck, E. M.; Liu, W., Spence, G. T.; Shaw, S. K.; Davis, A. P.; Destecroix, H.; Smith, B. D. Rapid Macrocycle Threading by a Fluorescent Dye-Polymer Conjugate in Water with Nanomolar Affinity. *J. Am. Chem. Soc.* 2015, 137, 8668-8671.

(25) Liu, W.; Peck, E. M.; Smith, B. D. High Affinity Macrocycle Threading by a Near-Infrared Croconaine Dye with Flanking Polymer Chains. *J. Phys. Chem. B* 2016, 120, 995-1001.

(26) Mohanty, J.; Nau, W. M. Ultrastable Rhodamine with Cucurbituril. *Angew. Chem. Int. Ed.* 2005, 44, 3750-3754.

(27) Liu, W.; Bobbala, S.; Stern, C. L.; Hornick, J. E.; Liu, Y.; Enciso, A. E.; Scott, E. A.; Stoddart, J. F. XCage: A Tricyclic Octacationic Receptor for Perylene Diimide with Picomolar Affinity in Water. *J. Am. Chem. Soc.* 2020, 142, 3165-3173.

(28) Schreiber, C. L.; Smith, B. D. Molecular Conjugation Using Non-Covalent Click Chemistry. *Nat. Rev. Chem.* 2019, 3, 393-400.

(29) Milgrom, L. R. *The Colours of Life: An introduction to the Chemistry of Porphyrins and Related Compounds*; Oxford University Press: Oxford New York Tokyo, 1997.

(30) Lombardi, A.; Nastri, F.; Pavone, V. Peptide-Based Heme-Protein Models. *Chem. Rev.* 2001, 101, 3165-3189.

(31) Reedy, C. J.; Gibney, B. R. Heme Protein Assemblies. *Chem. Rev.* 2004, 104, 617-649.

(32) Bois, P. S.; Anderson, H. L. Template-Directed Synthesis of Molecular Nanorings and Cages. *Acc. Chem. Res.* 2018, 51, 2083-2092.

(33) Yim, D.; Sung, J.; Kim, S.; Oh, J.; Yoon, H.; Sung, Y. M.; Kim, D.; Jang, W.-D. Guest-Induced Modulation of the Energy Transfer Process in Porphyrin-Based Artificial Light Harvesting Dendrimers. *J. Am. Chem. Soc.* 2016, 139, 993-1002.

(34) Liu, Y.; Jin, J.; Deng, H.; Li, K.; Zheng, Y.; Yu, C.; Zhou, Y. Protein-Framed Multi-Porphyrin Micelles for a Hybrid Natural-Artificial Light-Harvesting Nanosystem. *Angew. Chem. Int. Ed.* 2016, 55, 7952-7957.

(35) Omagari, T.; Suzuki, A.; Akita, M.; Yoshizawa, M. Efficient Catalytic Epoxidation in Water by Axial N-Ligand-Free Mn-Porphyrins within a Micellar Capsule. *J. Am. Chem. Soc.* 2016, 138, 499-502.

(36) Adam, S. M.; Wijeratne, G. B.; Rogler, P. J.; Diaz, D. E.; Quist, D. A.; Liu, J. J.; Karlin, K. D. Synthetic Fe/Cu Complexes: Toward Understanding Heme-Copper Oxidase Structure and Function. *Chem. Rev.* 2018, 118, 10840-11022.

(37) Kitagishi, H.; Tamaki, M.; Ueda, T.; Hirota, S.; Ohta, T.; Naruta, Y.; Kano, K. Oxoferryl Porphyrin/Hydrogen Peroxide System Whose Behavior Is Equivalent to Hydroperoxoferric Porphyrin. *J. Am. Chem. Soc.* 2010, 132, 16730-16732.

(38) Kano, K.; Kitagishi, H.; Kodera, M.; Hirota, S. Dioxygen Binding to a Simple Myoglobin Model in Aqueous Solution. *Angew. Chem. Int. Ed.* 2005, 44, 435-438.

(39) Merlau, M. L.; Mejia, M. D. P.; Nguyen, S. T.; Hupp, J. T. Artificial Enzymes Formed through Directed Assembly of Molecular Square Encapsulated Epoxidation Catalysts. *Angew. Chem. Int. Ed.* 2001, 40, 4239-4242.

(40) Elemans, J. A. A. W.; Nolte, R. J. M. Porphyrin Cage Compounds Based on Glycoluril—From Enzyme Mimics to Functional Molecular Machines. *Chem. Commun.* 2019, 55, 9590-9605.

(41) Rajora, M. A.; Lou, J. W. H.; Zheng, G. Advancing Porphyrin's Biomedical Utility via Supramolecular Chemistry. *Chem. Soc. Rev.* 2017, 46, 6433-6469.

(42) Ethirajan, M.; Chen, Y.; Joshi, P.; Pandey, R. K. The Role of Porphyrin Chemistry in Tumor Imaging and Photodynamic Therapy. *Chem. Soc. Rev.* 2011, 40, 340-362.

(43) Kundu, S.; Patra, A. Nanoscale Strategies for Light Harvesting. *Chem. Rev.* 2017, 117, 712-757.

(44) Galan, A.; Ballester, P. Stabilization of Reactive Species by Supramolecular Encapsulation. *Chem. Soc. Rev.* 2016, 45, 1720-1737.

(45) Polizzi, N. F.; Wu, Y.; Lemmin, T.; Maxwell, A. M.; Zhang, S. Q.; Rawson, J.; Beratan, D. N.; Therien, M. J.; DeGrado, W. F. De Novo Design of a Hyperstable Non-Natural Protein-Ligand Complex with Sub-Å Accuracy. *Nat. Chem.* 2017, 9, 1157-1164.

(46) Qi, Q.; Yang, C.; Xia, Y.; Guo, S.; Song, D.; Su, H. Preferential Binding of n-Ligand Porphyrin Targeting 5'-5' Stacking Interface of Human Telomeric RNA G-Quadruplex Dimer. *J. Phys. Chem. Lett.* 2019, 10, 2143-2150.

(47) Börjesson, K.; Wiberg, J.; El-Sagheer, A. H.; Ljungdahl, T.; Mårtensson, J.; Brown, T.; Nordén, B.; Albinsson, B. Functionalized Nanostructures: Redox-Active Porphyrin Anchors for Supramolecular DNA Assemblies. *ACS Nano.* 2010, 4, 5037-5046.

(48) Goto, Y., Sugikawa, K.; Ikeda, A. Enhancement in Guest Molecule Incorporation into Lipid Membranes in the Presence of Zinc-Porphyrin Anchor Molecules. *ChemixsrySelect* 2019, 4, 134-137.

(49) Synytsya, A.; Synytsya, A.; Blafkova, P.; Volka, K.; Král, V. Interaction of Meso-tetrakis(4-sulphonatophenyl) porphine with Chitosan in Aqueous Solutions. *Spectrochim. Acta Part A Mol. Biomol. Spectrosc.* 2007, 66, 225-235.

(50) Venema, F.; Rowan, A. E.; Nolte, R. J. M. Binding of Porphyrins in Cyclodextrin Dimers. *J. Am. Chem. Soc.* 1996, 118, 257-258.

(51) Pathak, P.; Yao, W.; Hook, K. D.; Vik, R.; Winnerdy, F. R.; Brown, J. Q.; Gibb, B. C.; Pursell, Z. F.; Phan, A. T.; Jayawickramarajah, J. Bright G-Quadruplex Nanostructures Functionalized with Porphyrin Lanterns. *J. Am. Chem. Soc.* 2019, 141, 12582-12591.

(52) Watanabe, K.; Kitagishi, H.; Kano, K. Supramolecular Iron Porphyrin/Cyclodextrin Dimer Complex that Mimics the Functions of Hemoglobin and Methemoglobin. *Angew. Chem. Int. Ed.* 2013, 52, 6894-6897.

(53) Moschetto, G.; Lauceri, R.; Gulino, F. G.; Sciotto, D.; Purrello, R. Non-Covalent Synthesis in Aqueous Solution of Discrete Multi-Porphyrin Aggregates with Programmable Stoichiometry and Sequence. *J. Am. Chem. Soc.* 2002, 124, 14536-14537.

(54) Kubota, R.; Takabe, T.; Arima, K.; Taniguchi, H.; Asayama, S.; Kawakami, H. New Class of Artificial Enzyme Composed of Mn-Porphyrin, Imidazole, and Cucurbit[10]Uril toward Use as a Therapeutic Antioxidant. *J. Mater. Chem. B* 2018, 6, 7050-7059.

(55) Liu, S.; Shukla, A. D.; Gadde, S.; Wagner, B. D.; Kaifer, A. E.; Isaacs, L. Ternary Complexes Comprising Cucurbit[10]uril, Porphyrins, and Guests. *Angew. Chem. Int. Ed.* 2008, 47, 2657-2660.

(56) Juriček, M.; Barnes, J. C.; Strutt, N. L.; Vermeulen, N. A.; Ghooray, K. C.; Dale, E. J.; McGonigal, P. R.; Blackburn, A. K.; Avestro, A.-J.; Stoddart, J. F. An ExBox [2]Catenane. *Chem. Soc.* 2014, 5, 2724.

(57) Roy, I.; Bobbala, S.; Young, R. M.; Beldjoudi, Y.; Nguyen, M. T.; Cetin, M. M.; Cooper, J. A.; Allen, S.; Anamimoghadam, O.; Scott, E. A.; Wasielewski, M. R.; Stoddart, J. F. A Supramolecular Approach for Modulated

(57) ...Photoprotection, Lysosomal Delivery, and Photodynamic Activity of a Photosensitizer. *J. Am. Chem. Soc.* 2019, 141, 12296-12304.

(58) Wu. Z. Q.; Li, C. Z.; Feng, D. J.; Jiang, X. K.; Li, Z. T. Foldamer-Based Pyridine-Fullerene Tweezer Receptors for Enhanced Binding of Zinc Porphyrin. *Tetrahedron* 2006, 62, 11054-11062.

(59) Ono, K.; Yoshizawa, M.; Kato, T.; Watanabe, K.; Fujita, M. Porphine Dimeric Assemblies in Organic-Pillared Coordination Cages. *Angew. Chem. Int. Ed.* 2007, 46, 1803-1806.

(60) Lefebvre, C.; Rubez, G.; Khartabil, H.; Boisson, J. C.; Contreras-Garcia, J.; Henon, E. Accurately Extracting the Signature of Intermolecular Interactions Present in The NCI Plot of The Reduced Density Gradient Versus Electron Density. *Phys. Chem. Chem. Phys.* 2017, 19, 17928-17936.

(63) Dempsey, J. M.; Zhai, C.; McGarraugh, H. H.; Schreiber, C. L.; Stoffel, S. E.; Johnson, A.; Smith, B. D. High Affinity Threading of a New Tetralactam Macrocycle in Water by Fluorescent Deep-Red and near-Infrared Squaraine Dyes. *Chem. Commun.* 2019, 55, 12793-12796.

(64) Cheng, C.; Cheng, T.; Xiao, H.; Krzyaniak, M. D.; Wang, Y.; McGonigal, P. R.; Frasconi, M.; Barnes, J. C.; Fahrenbach, A. C.; Wasielewski, M. R.; Goddard III, W. A.; Stoddart, J. F. Influence of Constitution and Charge on Radical Pairing Interactions in Tris-Radical Tricationic Complexes. *J. Am. Chem. Soc.* 2016, 138, 8288-8300.

(66) Dale, E. J.; Vermeulen, N. A.; Thomas, A. A.; Barnes, J. C.; Juriček, M.; Blackburn, A. K.; Strutt, N. L.; Sarjeant, A. A., Stern, C. L.; Denmark, S. E.; Stoddart, J. F. ExCage. *J. Am. Chem. Soc.* 2014, 136, 10669-10682.

(68) Ghosh, I.; Nau, W. M. The Strategic Use of Supramolecular pKa Shifts to Enhance the Bioavailability of Drugs. *Adv. Drug Deliv. Rev.* 2012, 64, 764-783.

(69) Pluth, M. D.; Bergman, R. G.; Raymond, K. N. Making Amines Strong Bases: Thermodynamic Stabilization of Protonated Guests in a Highly-Charged Supramolecular Host. *J. Am. Chem. Soc.* 2007, 129, 11459-11467.

(70) Saleh, N.; Koner, A. L.; Nau, W. M. Activation and Stabilization of Drugs by Supramolecular pKa Shifts: Drug-Delivery Applications Tailored for Cucurbiturils. *Angew. Chem. Int. Ed.* 2008, 47, 5398-5401.

(71) Wolter, A. C.; Weickhmann, A. K.; Nasiri, A. H.; Hantke, K.; Ohlenschläger, O.; Wunderlich, C. H.; Kreutz, C.; Duchardt-Ferner, E.; Wöhnert, J. A Stably Protonated Adenine Nucleotide with a Highly Shifted $pK_a$ Value Stabilizes the Tertiary Structure of a GTP-Binding RNA Aptamer. *Angew. Chem. Int. Ed.* 2017, 56, 401-404.

(72) Yin, H.; Cheng, Q.; Rosas, R.; Viel, S.; Monnier, V.; Charles, L.; Siri, D.; Gigmes, D.; Ouari, O.; Wang, R.; Kermagoret, A.; Bardelang, D. A Cucurbit[8]uril 2:2 Complex with a Negative pKa Shift. *Chem. Eur. J.* 2019, 25, 12552-12559.

(73) A control study was performed using Porp-211 which was dissolved in $CD_3OD$. We found that more than 99.9% of the NH signal at −3.2 ppm undergoes exchange to ND.

(74) Sedghi, G.; Sawada, K.; Esdaile, L. J.; Hoffmann, M.; Anderson, H. L.; Bethell, D.; Haiss, W.; Higgins, S. J.; Nichols, R. J. Single Molecule Conductance of Porphyrin Wires with Ultralow Attenuation. *J. Am. Chem. Soc.* 2008, 130, 8582-8583.

(75) Li, Z.; Borguet, E. Determining Charge Transport Pathways through Single Porphyrin Molecules Using Scanning Tunneling Microscopy Break Junctions. *J. Am. Chem. Soc.* 2012, 134, 63-66.

(76) Zhu, S. E.; Kuang, Y. M.; Geng, F.; Zhu, J. Z.; Wang, C. Z.; Yu, Y. J.; Luo, Y.; Xiao, Y.; Liu, K. Q.; Meng, Q. S.; Zhang, L.; Jiang, S.; Zhang, Y.; Wang, G. W.; Dong, Z. C.; Hou, J. G. Self-Decoupled Porphyrin with a Tripodal Anchor for Molecular-Scale Electroluminescence. *J. Am. Chem. Soc.* 2013, 135, 15794-15800.

(77) Wang, A.; Ye, J.; Humphrey, M. G.; Zhang, C. Graphene and Carbon-Nanotube Nanohybrids Covalently Functionalized by Porphyrins and Phthalocyanines for Optoelectronic Properties. *Adv. Mater.* 2018, 30, 1-9.

(78) Kesters, J.; Verstappen, P.; Kelchtermans, M.; Lutsen, L.; Vanderzande, D.; Maes, W. Porphyrin-Based Bulk Heterojunction Organic Photovoltaics: The Rise of the Colors of Life. *Adv. Energy Mater.* 2015, 5, 1-20.

(79) Otsuki, J. Supramolecular Approach towards Light-Harvesting Materials Based on Porphyrins and Chlorophylls. *J. Mater. Chem. A* 2018, 6, 6710-6753.

(80) Xue, X.; Lindstrom, A.; Li, Y. Porphyrin-Based Nanomedicines for Cancer Treatment. *Bioconjug. Chem.* 2019, 30, 1585-1603.

(S1) Liu, W.; Bobbala, S.; Stern, C. L.; Homick, J. E.; Liu, Y.; Enciso, A. E.; Scott, E. A.; Stoddart, J. F. XCage: A Tricyclic Octacationic Receptor for Perylene Diimide with Picomolar Affinity in Water. *J. Am. Chem. Soc.* 2020, 142, 3165-3173.

(S2) Ryan, S. T. J.; Del Barrio, J.; Ghosh, I.; Biedermann, F.; Lazar, A. I.; Lan, Y.; Coulston, R. J.; Nau, W. M.; Scherman, O. A. Efficient Host-Guest Energy Transfer in Polycationic Cyclophane-Perylene Diimide Complexes in Water. *J. Am. Chem. Soc.* 2014, 136, 9053-9060.

(S3) Kuang, G.; Zhang, Q.; Li, D. Y.; Shang, X. S.; Lin, T.; Liu, P. N.; Lin, N. Cross-Coupling of Aryl-Bromide and Porphyrin-Bromide on an Au(111) Surface. *Chem. Eur. J.* 2015, 21, 8028-8032.

(S4) Song, X. Z.; Jaquinod, L.; Jentzen, W.; Nurco, D. J.; Jia, S. L.; Khoury, R. G.; Ma, J. G.; Medforth, C. J.; Smith, K. M.; Shelnutt, J. A. Metal Dependence of the Contributions of Low-Frequency Normal Coordinates to the Sterically Induced Distortions of Meso-Dialkyl-Substituted Porphyrins. *Inorg. Chem.* 1998, 37, 2009-2019.

(S5) Dolomanov, O. V; Bourhis, L. J.; Gildea, R. J.; Howard, J. A. K.; Puschmann, H. OLEX2: A Complete Structure Solution, Refinement and Analysis Program. *J. Appl. Crystallogr.* 2009, 42, 339-341.

(S6) Sheldrick, G. M. SHELXT-Integrated Space-Group and Crystal-Structure Determination. *Acta Crystallogr. Sect. A* 2015, 71, 3-8.

(S7) Sheldrick, G. M. A Short History of SHELX. *Acta Crystallogr. Sect. A* 2008, 64, 112-122.

(S8) Thom, A.; Dittrich, B.; Sheldrick, G. M. Enhanced Rigid-Bond Restraints. *Acta Crystallogr. Sect. A* 2012, 68, 448-451.

(S9) MOPAC. MOPAC2016, James J. P. Stewart, Stewart Comput. Chem. Color. Springs, CO, USA, HTTP//Open-MOPAC.net (2016).

(S10) Lefebvre, C.; Rubez, G.; Khartabil, H.; Boisson, J. C.; Contreras-Garcia, J.; Hénon, E. Accurately Extracting The Signature of Intermolecular Interactions Present in The NCI Plot of The Reduced Density Gradient Versus Electron Density. *Phys. Chem. Chem. Phys.* 2017, 19, 17928-17936.

(S11) Lu, T.; Chen, F. Multiwfn: A Multifunctional Wavefunction Analyzer. *J. Comput. Chem.* 2012, 33, 580-592.

(S12) Pettersen, E. F.; Goddard, T. D.; Huang, C. C.; Couch, G. S.; Greenblatt, D. M.; Meng, E. C.; Ferrin, T. E. UCSF Chimera—A Visualization System for Exploratory Research and Analysis. *J. Comput. Chem.* 2004, 25, 1605-1612.

(S13) Dale, E. J.; Vermeulen, N. A.; Thomas, A. A.; Barnes, J. C.; Juriček, M.; Blackburn, A. K.; Strutt, N. L.; Sarjeant, A. A.; Stern, C. L.; Denmark, S. E.; Stoddart, J. F. ExCage. *J. Am. Chem. Soc.* 2014, 136, 10669-10682.

(S14) Roy, 1.; Bobbala, S.; Young, R. M.; Beidjoudi, Y.; Nguyen, M. T.; Cetin, M. M.; Cooper, J. A.; Allen, S.; Anamimoghadam, O.; Scott, E. A.; Wasielewski, M. R.; Stoddart. J. F. A Supramolecular Approach for Modulated Photoprotection, Lysosomal Delivery, and Photodynamic Activity of a Photosensitizer. *J. Am. Chem. Soc.* 2019, 141, 12296-12304.

(S15) Thordarson, P. Determining Association Constants from Titration Experiments in Supramolecular Chemistry. *Chem. Soc. Rev.* 2011, 40, 1305-1323.

(S16) Hargrove, A. E.; Zhong, Z.; Sessler, J. L.; Anslyn, E. V. Algorithms for the Determination of Binding Constants and Enantiomeric Excess in Complex Host: Guest Equilibria Using Optical Measurements. *New J. Chem.* 2010, 34, 348.

(S17) Peck, E. M.; Liu, W.; Spence, G. T.; Shaw, S. K.; Davis, A. P.; Destecroix, H.; Smith, B. D. Rapid Macrocycle Threading by a Fluorescent Dye-Polymer Conjugate in Water with Nanomolar Affinity. *J. Am. Chem. Soc.* 2015, 137, 86684671.

We claim:

1. A receptor-substrate complex, or a salt thereof, the complex comprising a tricyclic octacationic cyclophane and a pyrrole dye complexed therein, wherein the cyclophane is

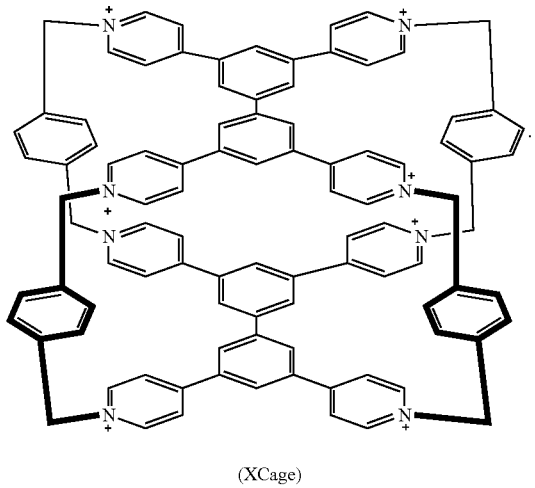

(XCage)

2. The complex of claim 1, wherein the pyrrole dye is a porphyrin dye.

3. The complex of claim 1, wherein the pyrrole dye is a metalloporphyrin dye.

4. The complex of claim 1, wherein the pyrrole dye has a formula

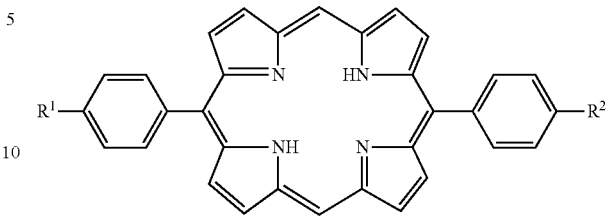

wherein $R^1$ and $R^2$ are independently selected from hydrogen, —OH, —NRR', —$NO_2$, —SH, —SR, —R, —OR, —COOR, —$OCH_2CH_2(OCH_2CH_2)_n$—OR, or —$OCH_2$-(triazole)-$CH_2CH_2$—$(OCH_2CH_2)_n$—OR, wherein each R and R' are independently selected from a substituted or unsubstituted, branched or unbranched, saturated or unsaturated $C_1$-$C_6$ alkyl, and wherein n is an integer greater than or equal to zero.

5. The complex of claim 1, wherein the pyrrole dye has a formula

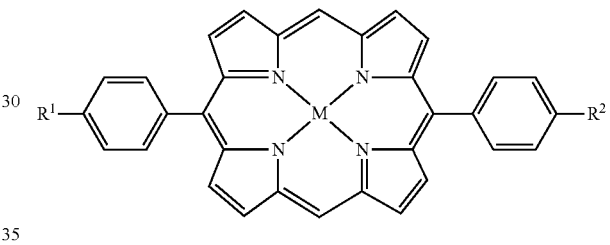

wherein $R^1$ and $R^2$ are independently selected from hydrogen, —OH, —NRR', —$NO_2$, —SH, —SR, —R, —OR, —COOR, —$OCH_2CH_2(OCH_2CH_2)_n$—OR, or —$OCH_2$-(triazole)-$CH_2CH_2$—$(OCH_2CH_2)_n$—OR, wherein each R and R' are independently selected from a substituted or unsubstituted, branched or unbranched, saturated or unsaturated $C_1$-$C_6$ alkyl, wherein n is an integer greater than or equal to zero, and wherein M is a transition metal or an alkaline earth metal.

6. A salt comprising the complex according to claim 1 and a counter anion.

7. The salt of claim 6, wherein the counter anion is $CF_3CO_2^{31}$, $PF_6^-$, or $Cl^-$.

8. A crystalline composition comprising the complex of claim 1.

9. The crystalline composition of claim 8, wherein the crystalline composition has a triclinic, space group P-1 (no. 2) crystal parameter and wherein the crystalline composition has unit cell parameters: a=14.7±0.1 Å, b=17.5±0.1 Å, c=19.1±0.1 Å, α=109.0±0.1°, β=106.7±0.1°, and γ=102.3±0.1°.

10. The crystalline composition of claim 8, wherein the crystalline composition has a triclinic, space group P-1 (no. 2) crystal parameter and wherein the crystalline composition has unit cell parameters: a=14.7±0.1 Å, b=17.5±0.1 Å, c=19.0±0.1 Å, α=108.9±0.1°, β=106.7±0.1°, and γ=102.1±0.1°.

11. A method for fluorescence spectroscopy, comprising providing the complex according to claim 1, irradiating the complex with an irradiation source, and detecting an emission signal from the complex.

12. The method of claim 11 further comprising providing a dye and detecting an emission signal from the dye.

13. The method of claim 12, wherein the complex and the dye are irradiated by the same irradiation source and wherein the emission signal of the complex and the emission signal of the dye are detectably distinct.

14. The method of claim 11, wherein the complex is localized in an aqueous environment.

15. A method for stabilizing a pyrrole dye, the method comprising providing a tricyclic octacationic cyclophane and complexing the cyclophane with the pyrrole dye to prepare the receptor-substrate complex according to claim 1.

16. The method of claim 15, wherein the pyrrole dye resists protonation in an aqueous environment.

17. The method of claim 15, wherein the pyrrole dye resists NH proton exchange with a pyrrole core in an aqueous environment.

18. The method of claim 15, wherein the pyrrole dye resists solvolysis in an aqueous environment.

19. A method for preparing the receptor-substrate complex of claim 1, the method comprising providing the tricyclic octacationic cyclophane, providing a pyrrole dye, and contacting the tricyclic octacationic cyclophane and the pyrrole dye.

20. The complex of claim 1, wherein the pyrrole dye is a chlorin, a bacteriochlorin, a phthalocyanine, a naphthalocyanine, or a subphthalocyanine.

21. The complex of claim 5, wherein M is Au, Pd, Pt, Cu, Ni, Mg, Fe, Mn, or Co.

* * * * *